(12) United States Patent
Moturu et al.

(10) Patent No.: US 10,265,028 B2
(45) Date of Patent: Apr. 23, 2019

(54) METHOD AND SYSTEM FOR MODELING BEHAVIOR AND HEART DISEASE STATE

(71) Applicant: Ginger.io, Inc., San Francisco, CA (US)

(72) Inventors: Sai Moturu, San Francisco, CA (US); Anmol Madan, San Francisco, CA (US)

(73) Assignee: Ginger.io, Inc., San Francisco, CA (US)

( * ) Notice: Subject to any disclaimer, the term of this patent is extended or adjusted under 35 U.S.C. 154(b) by 295 days.

(21) Appl. No.: 15/245,571

(22) Filed: Aug. 24, 2016

(65) Prior Publication Data

US 2017/0000422 A1    Jan. 5, 2017

Related U.S. Application Data

(63) Continuation-in-part of application No. 14/839,232, filed on Aug. 28, 2015, now Pat. No. 10,068,060, (Continued)

(51) Int. Cl.
*A61B 5/00*   (2006.01)
*A61B 5/0205* (2006.01)
(Continued)

(52) U.S. Cl.
CPC .......... *A61B 5/7275* (2013.01); *A61B 5/0022* (2013.01); *A61B 5/0205* (2013.01); (Continued)

(58) Field of Classification Search
None
See application file for complete search history.

(56) References Cited

U.S. PATENT DOCUMENTS 6,356,940 B1   3/2002  Short
7,188,151 B2   3/2007  Kumar et al.
(Continued)

FOREIGN PATENT DOCUMENTS

CN    101600008 A    12/2009
JP   2010514497 A     5/2010
(Continued)

*Primary Examiner* — Michael Tomaszewski
(74) *Attorney, Agent, or Firm* — Jeffrey Schox

(57) ABSTRACT

A method for evaluating cardiovascular health of a patient includes receiving a log of use dataset associated with patient digital communication behavior at a mobile computing device, wherein the log of use dataset is associated with a time period, receiving a supplementary dataset associated with the time period, generating a survey dataset based on a patient response to a survey, generating a cardiovascular health predictive model based upon at least one of the log of use dataset, the supplementary dataset, and the survey dataset, extracting a cardiovascular health metric from at least one of an output of the cardiovascular health predictive model, the log of use dataset, the supplementary dataset, and the survey dataset, wherein the cardiovascular health metric is associated with the time period; providing a cardiovascular-related notification to the patient; and automatically providing a cardiovascular therapeutic intervention at a cardiovascular device for the patient.

21 Claims, 10 Drawing Sheets

Related U.S. Application Data which is a continuation-in-part of application No. 13/969,339, filed on Aug. 16, 2013, now abandoned.

(60) Provisional application No. 61/683,867, filed on Aug. 16, 2012, provisional application No. 61/683,869, filed on Aug. 16, 2012, provisional application No. 62/212,069, filed on Aug. 31, 2015.

(51) Int. Cl.
| | | |
|---|---|---|
| *G16H 50/50* | (2018.01) | |
| *G16H 10/20* | (2018.01) | |
| *G16H 50/20* | (2018.01) | |
| *G16H 20/30* | (2018.01) | |
| *G16H 20/13* | (2018.01) | |
| *G16H 20/70* | (2018.01) | |
| *A61B 5/11* | (2006.01) | |
| *A61B 5/021* | (2006.01) | |
| *A61B 5/024* | (2006.01) | |
| *A61B 5/08* | (2006.01) | |
| *A61M 21/00* | (2006.01) | |
| *G16H 40/67* | (2018.01) | |

(52) U.S. Cl.
CPC .......... *A61B 5/4836* (2013.01); *A61B 5/7278* (2013.01); *G16H 10/20* (2018.01); *G16H 20/13* (2018.01); *G16H 20/30* (2018.01); *G16H 20/70* (2018.01); *G16H 50/20* (2018.01); *G16H 50/50* (2018.01); *A61B 5/021* (2013.01); *A61B 5/024* (2013.01); *A61B 5/0816* (2013.01); *A61B 5/1118* (2013.01); *A61M 2021/0027* (2013.01); *G16H 40/67* (2018.01)

(56) References Cited

U.S. PATENT DOCUMENTS

| | | | |
|---|---|---|---|
| 7,246,677 B2 | 7/2007 | Fredriksson et al. | |
| 7,248,677 B2 | 7/2007 | Randall et al. | |
| 7,337,158 B2 | 2/2008 | Fratkina et al. | |
| 7,376,700 B1 | 5/2008 | Clark et al. | |
| 7,761,309 B2 | 7/2010 | Sacco et al. | |
| 8,160,901 B2 | 4/2012 | Heywood et al. | |
| 8,684,922 B2 | 4/2014 | Tran | |
| 9,286,442 B2 | 3/2016 | Csoma et al. | |
| 9,294,403 B2 | 3/2016 | Mejia et al. | |
| 9,684,922 B2 | 6/2017 | Elberbaum | |
| 2002/0198473 A1 | 12/2002 | Kumar et al. | |
| 2004/0078223 A1 | 4/2004 | Sacco et al. | |
| 2004/0225340 A1 | 11/2004 | Evans | |
| 2005/0020903 A1 | 1/2005 | Krishnan et al. | |
| 2005/0055321 A1 | 3/2005 | Fratkina et al. | |
| 2005/0108051 A1 | 5/2005 | Weinstein | |
| 2005/0169446 A1 | 8/2005 | Randall et al. | |
| 2006/0064037 A1 | 3/2006 | Shalon et al. | |
| 2007/0094048 A1* | 4/2007 | Grichnik | G06Q 50/22 705/2 |
| 2007/0226012 A1 | 9/2007 | Salgado et al. | |
| 2007/0288266 A1 | 12/2007 | Sysko et al. | |
| 2008/0059570 A1 | 3/2008 | Bill | |
| 2009/0125333 A1 | 5/2009 | Heywood et al. | |
| 2010/0082367 A1* | 4/2010 | Hains | G06F 19/3456 705/2 |
| 2010/0203876 A1 | 8/2010 | Krishnaswamy | |
| 2011/0009715 A1 | 1/2011 | Karplus et al. | |
| 2011/0066036 A1 | 3/2011 | Zilca et al. | |
| 2011/0119212 A1 | 5/2011 | De et al. | |
| 2011/0184250 A1 | 7/2011 | Schmidt et al. | |
| 2012/0053425 A1 | 3/2012 | Michelson et al. | |
| 2012/0289791 A1 | 11/2012 | Jain et al. | |
| 2013/0004129 A1 | 1/2013 | Zhang | |
| 2013/0042116 A1 | 2/2013 | Sakumoto | |
| 2013/0085758 A1 | 4/2013 | Csoma et al. | |
| 2013/0095459 A1 | 4/2013 | Tran | |
| 2013/0117040 A1 | 5/2013 | James et al. | |
| 2013/0154838 A1 | 6/2013 | Alameh et al. | |
| 2013/0246330 A1 | 9/2013 | Son et al. | |
| 2013/0297536 A1* | 11/2013 | Almosni | G16H 50/20 706/12 |
| 2014/0039914 A1 | 2/2014 | Dansereau et al. | |

FOREIGN PATENT DOCUMENTS

| | | |
|---|---|---|
| WO | 2008085308 A1 | 7/2008 |
| WO | 2008096634 A1 | 8/2008 |
| WO | 2012025622 A2 | 3/2012 |
| WO | 2015003247 A1 | 1/2015 |

\* cited by examiner

METHOD AND SYSTEM FOR MODELING BEHAVIOR AND HEART DISEASE STATE

CROSS-REFERENCE TO RELATED APPLICATIONS

This application is a continuation-in-part application of U.S. application Ser. No. 14/839,232 filed 28 Aug. 2015, which is a continuation-in-part application of U.S. application Ser. No. 13/969,339 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application also claims the benefit of U.S. Provisional Application Ser. No. 62/212,069 filed 31 Aug. 2015, which is incorporated in its entirety herein by this reference.

TECHNICAL FIELD

This invention relates generally to the field of patient health and more specifically to a new and useful method for modeling behavior and heart disease state in the field of patient health.

DESCRIPTION OF THE EMBODIMENTS

The following description of the embodiments of the invention is not intended to limit the invention to these embodiments, but rather to enable any person skilled in the art to make and use this invention.

1. Overview.

Figure 1:
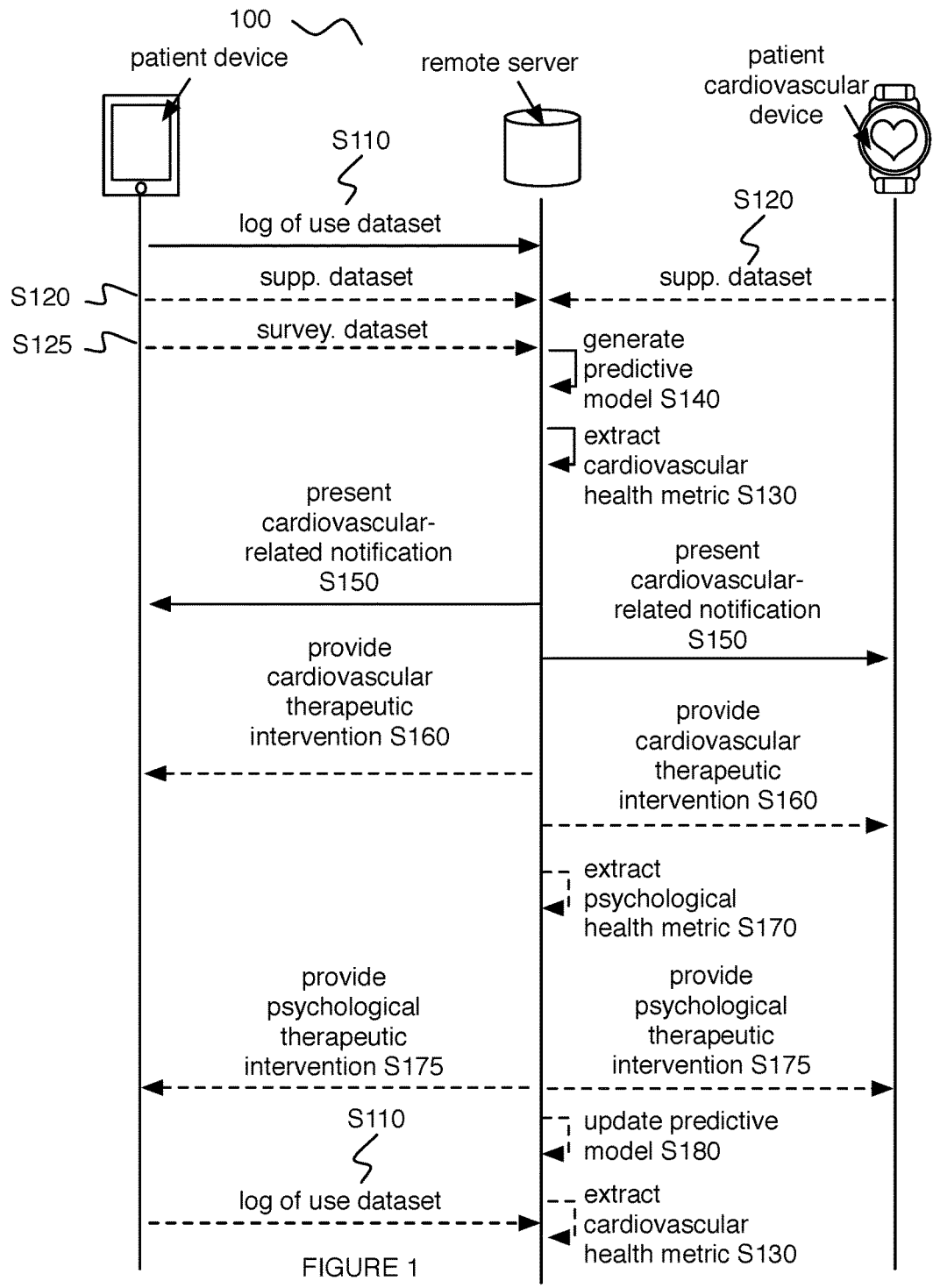
FIG. 1 is a flowchart representation of an embodiment of a method.
Figure 3:
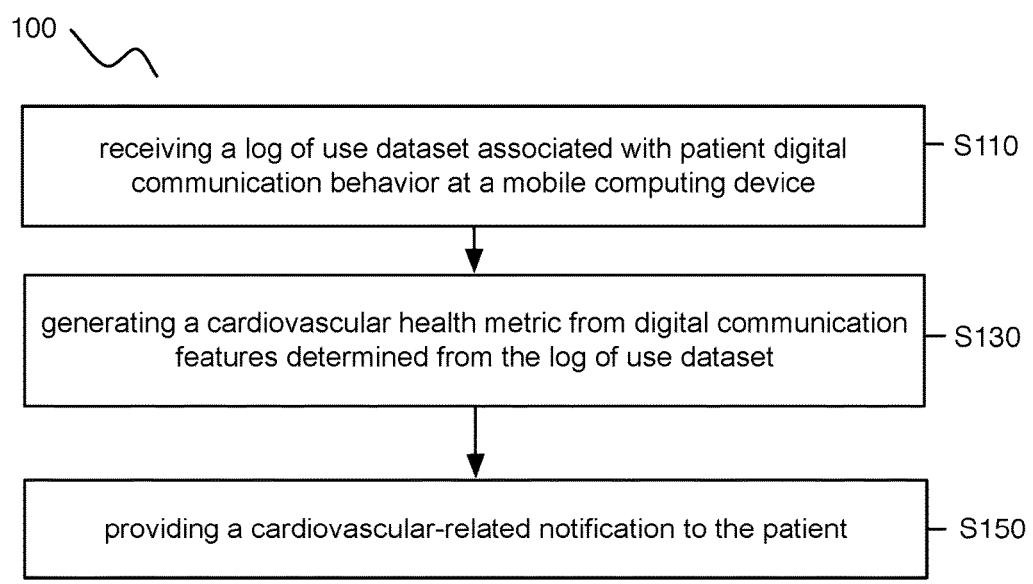
FIG. 3 is a flowchart representation of a variation of an embodiment of the method.
Figure 4:
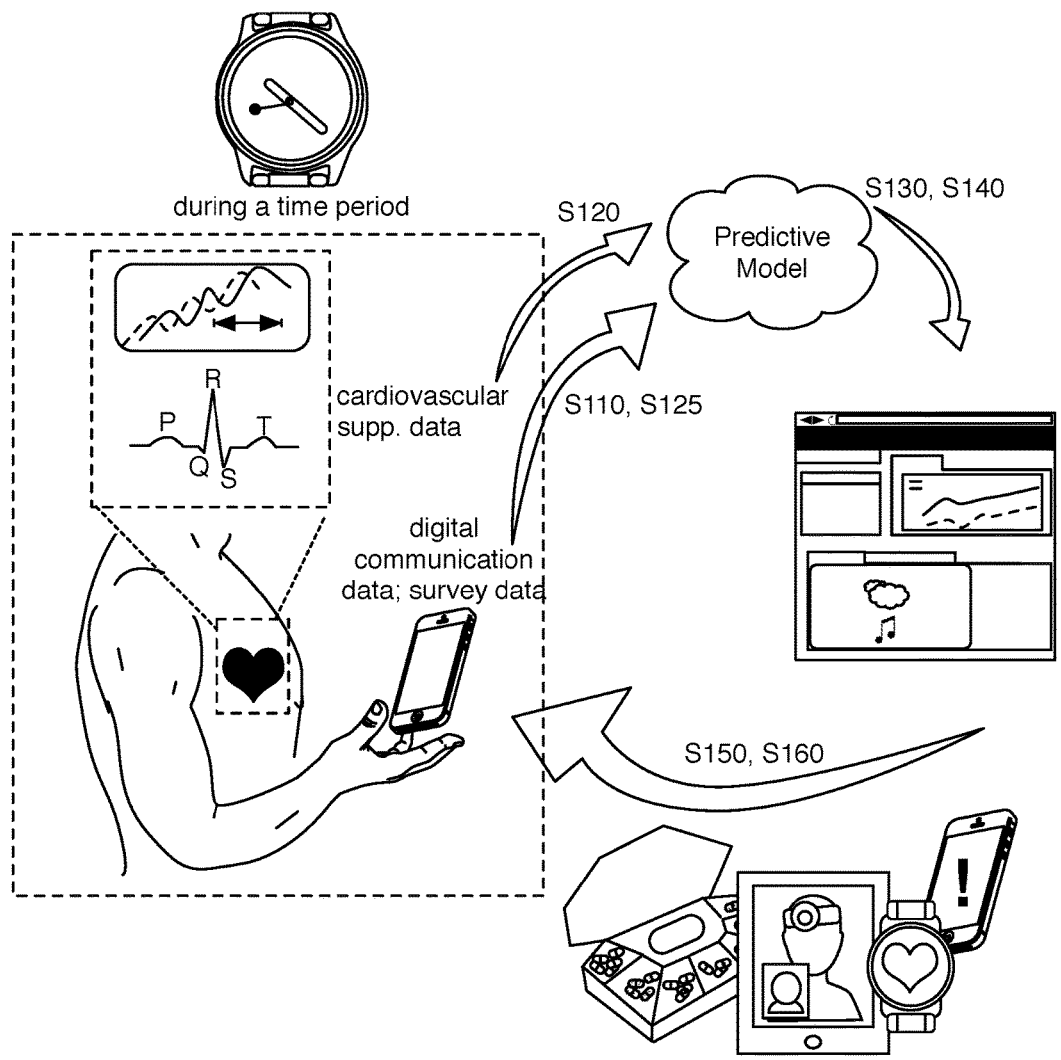
FIG. 4 is a schematic representation of a variation of an embodiment of the method.

As shown in FIGS. 1, 3, and 4, an embodiment of a method 100 for evaluating cardiovascular health of a patient includes receiving a log of use dataset associated with patient digital communication behavior at a mobile computing device S110; generating a cardiovascular health metric from digital communication behavior features determined from the log of use dataset S130; and providing a cardiovascular-related notification to the patient, based on the cardiovascular health metric S150.

Figure 2:
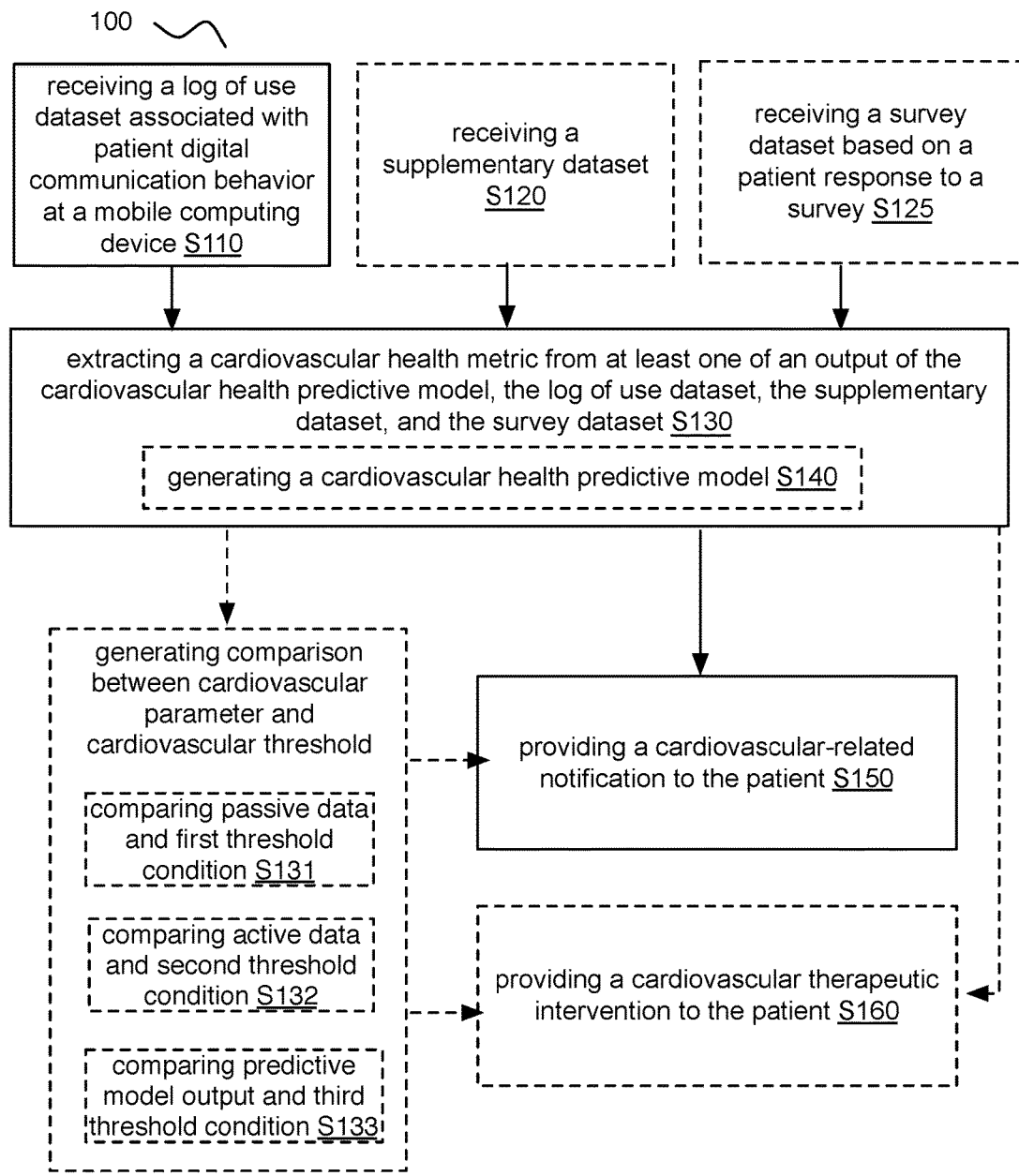
FIG. 2 is a flowchart representation of a variation of an embodiment of the method.

In a variation, as shown in FIGS. 1, 2, and 4, a method 100 for evaluating cardiovascular health of a patient includes receiving a log of use dataset associated with patient digital communication behavior at a mobile computing device, wherein the log of use dataset is associated with a time period S110; receiving a supplementary dataset associated with the time period S120; generating a survey dataset based on a patient response to a survey, wherein the survey dataset is associated with the time period S125; generating a cardiovascular health predictive model based upon at least one of the log of use dataset, the supplementary dataset, and the survey dataset S140; extracting a cardiovascular health metric from at least one of an output of the cardiovascular health predictive model, the log of use dataset, the supplementary dataset, and the survey dataset, wherein the cardiovascular health metric is associated with the time period S130; providing a cardiovascular-related notification to the patient S150; and automatically providing a cardiovascular therapeutic intervention for the patient S160.

The method 100 functions to analyze digital communication behaviors and/or other information (e.g., location data, cardiovascular device data, survey data) regarding a patient (e.g., a user, an at-risk individual) in order to evaluate the cardiovascular health of the patient. Additionally or alternatively, the method 100 can function to initiate automatic provision of a cardiovascular therapeutic intervention (e.g., at a cardiovascular care device, at a mobile computing device, etc.) designed to improve a patient's cardiovascular health.

As such, the method 100 can facilitate cardiovascular monitoring, treatment, and/or treatment response evaluation for any suitable patient. In particular, the method 100 can be used to monitor and/or treat cardiovascular disease patients who are suffering from and/or at-risk for any one or more of: rheumatic heart disease, hypertensive heart disease, coronary artery disease, congestive heart failure, cerebrovascular disease, inflammatory heart disease, cardiomyopathy, heart arrhythmia, congenital heart disease, valvular heart disease, carditis, aortic aneurysms, peripheral artery disease, venous thrombosis, myocardial infarction, angina, aneurysm, hypertension, atherosclerosis, stroke, transient ischemic attacks, pericardial disease, and/or any other suitable cardiovascular condition. Additionally or alternatively, the method 100 can enable evaluation of patients suffering from cardiovascular disease-related symptoms including any one or more of: aching, breathlessness, burning, cramping, discomfort, fullness, heaviness, indigestion, lightheadedness, nausea, numbness, tinging, pain, pressure, shortness of breath, sweating, dizziness, squeezing, tightness, vomiting, irregular heartbeat, palpitations, chest pounding, fatigue, weakness, and/or any other suitable symptoms.

2. Benefits.

In specific examples, the method 100 and/or system 200 can confer several benefits over conventional methodologies used for evaluating cardiovascular health and/or providing cardiovascular health therapies. However, In specific examples, the method 100 and/or system 200 can perform one or more of the following:

First, the technology can implement tools that unobtrusively evaluate cardiovascular health. The technology can leverage passively collected digital communication data (e.g., text messaging characteristics, phone calling characteristics) and correlations between digital communication behaviors and cardiovascular health, in order to infer one or more cardiovascular health parameters for a patient. Such digital communication data can be collected from a patient's mobile phone, smart watch, laptop, and/or other suitable patient device. Additionally or alternatively, the technology can augment the cardiovascular health monitoring process with passively collected supplementary data (e.g., location data, cardiovascular device data and/or actively collected data (e.g., responses to digital surveys). However, the technology can output accurate measurements of cardiovascular health while requiring a minimal or otherwise reduced amount of effort by a patient.

Second, the technology can provide a variety of therapeutic interventions configured to improve the cardiovascular health of a patient. Therapeutic interventions (e.g., telemedicine, notifications, controlling operation of a patient device, etc.) can be automatically provided through any suitable patient device. Further, therapeutic interventions can be personalized for a given patient (e.g., based on patient demographic, patient feedback, cardiovascular health metrics generated for the patient, etc.). Patient responses to therapeutic intervention can be monitored, evaluated, and used to modify a therapeutic intervention regimen. As such, the technology can provide a full-stack approach to cardiovascular health, including patient monitoring, treatment, and treatment response evaluation.

Third, the technology can improve the technical fields of at least digital communication, and computational modeling of behavior and heart disease state. The technology can continuously collect and utilize datasets unique to internet-enabled mobile computing devices (e.g., social network usage, text messaging characteristics, application usage, patient response monitoring data facilitated through the mobile computing device, etc.) in order to provide real-time cardiovascular health monitoring and/or cardiovascular therapeutic intervention. Further, the technology can take advantage of such patient digital communication datasets to better improve the understanding of correlations between patient digital communication behavior and cardiovascular health, leading to an increased understanding of cardiovascular disease.

Fourth, the technology can provide technical solutions necessarily rooted in computer technology (e.g., utilizing computer models to extract cardiovascular health insights from datasets unique to internet-enabled mobile computing devices, in order to provide real-time cardiovascular health monitoring and/or interventions at devices for improving cardiovascular health or otherwise automatically providing cardiovascular health improving interventions, etc.) to overcome issues specifically arising with computer technology (e.g., issues surrounding how to use a plethora of passively collected patient digital communication data and/or actively collected data to promote cardiovascular health).

Fifth, the technology can leverage specialized computing devices (e.g., computing devices with GPS location and/or physical activity monitoring functionality, cardiovascular therapy devices, cardiovascular monitoring devices, etc.) to collect specialized datasets for determining cardiovascular health metrics and/or to provide therapeutic interventions based on collected data and/or generated metrics.

The technology can, however, provide any other suitable benefit(s) in the context of using non-generalized computer systems for evaluating cardiovascular health and/or providing cardiovascular therapeutic interventions.

3. Method.

As shown in FIGS. 1, 2, and 4, a method 100 for evaluating cardiovascular health of a patient includes receiving a log of use dataset associated with patient digital communication behavior at a mobile computing device, wherein the log of use dataset is associated with a time period S110; receiving a supplementary dataset associated with the time period S120; generating a survey dataset based on a patient response to a survey, wherein the survey dataset is associated with the time period S125; generating a cardiovascular health predictive model based upon at least one of the log of use dataset, the supplementary dataset, and the survey dataset S140; extracting a cardiovascular health metric from at least one of an output of the cardiovascular health predictive model, the log of use dataset, the supplementary dataset, and the survey dataset, wherein the cardiovascular health metric is associated with the time period S130; providing a cardiovascular-related notification to the patient S150; and automatically providing a cardiovascular therapeutic intervention for the patient S160.

The method 100 can additionally or alternatively include generating a psychological health metric S170; promoting a psychological therapeutic intervention S175; and/or updating a predictive model S180.

The method 100 is preferably implemented at least in part by an embodiment of the system 200 described in Section 4 below, variations of which can be implemented at least in part by embodiments, variations, and examples of the system described in U.S. application Ser. No. 13/969,339 entitled "Method for Modeling Behavior and Health Changes" and filed on 16 Aug. 2013; however, the method 100 can alternatively be implemented using any other suitable system configured to process communication and/or other behavior of the patient, in aggregation with other information, in order to generate a model of behavior and cardiovascular health in the patient.

3.1 Passive Data—Receiving a Log of Use Dataset.

As shown in FIGS. 1-4, Block S110 recites: receiving a log of use dataset associated with patient digital communication behavior at a mobile computing device. Block S110 functions to unobtrusively collect and/or retrieve communication-related data from a patient's mobile communication device. Preferably, Block S110 is implemented using a module of a computing system configured to interface with a native data collection application executing on a mobile communication device (e.g., smartphone, tablet, personal data assistant (PDA), personal music player, vehicle, head-mounted wearable computing device, wrist-mounted wearable computing device, etc.) of the patient, in order to retrieve patient communication data. As such, in one variation, a native data collection application can be installed on the mobile communication device of the patient, can execute substantially continuously while the mobile communication device is in an active state (e.g., in use, in an on-state, in a sleep state, etc.), and can record communication parameters (e.g., communication times, durations, contact entities, etc.) of each inbound and/or outbound communication (e.g., call, message) from the mobile communication device. In implementing Block S110, the mobile communication device can then upload this data to a database (e.g., remote server, cloud computing system, storage module), at a desired frequency (e.g., in near real-time, every hour, at the end of each day, etc.) to be accessed by the computing system. In one example of Block S110, the data collection application can launch on the patient's mobile communication device as a background process that gathers patient data once the patient logs into an account, wherein the patient data includes how and with what frequency the patient interacts with and communicates with other individuals through phone calls, e-mail, instant messaging, an online social network, and any other suitable mode of communication.

In relation to Block S110, a digital communication dataset is preferably associated with a temporal indicator (e.g., time point, time window, time period, minute, hour, day, month, etc.) indicating when the digital communications occurred. However, a digital communication dataset can be distinct from temporal indicators. Collecting a digital communication dataset is preferably performed prior to generating a cardiovascular health metric S130, but can additionally or alternatively be performed before, during, in response to, and/or after any suitable portion of the method 100, and/or at any suitable time. In a variation, Block S110 can include collecting a digital communication dataset during a time period in which a supplementary dataset and/or a survey dataset was collected. For example, a digital communication dataset and a supplementary dataset can correspond to a same or overlapping time period. Datasets corresponding to a same and/or overlapping time period can be used in generating a cardiovascular health metric describing cardiovascular health for the patient during the time period. Alternatively, datasets can correspond to different time periods, and/or have any suitable temporal association. In another variation, Block S110 can include collecting a digital communication dataset during, in response to, and/or after a cardiovascular treatment (e.g., a cardiovascular therapeutic intervention provided in Block S160). Digital communication datasets collected during such a time period can enable evaluation of a treatment response by a treatment response model.

Regarding Block S110, in accessing the log of use of the native communication application and receiving the log of use dataset, Block S110 preferably enables collection of one or more of: phone call-related data (e.g., number of sent and/or received calls, call duration, call start and/or end time, location of patient before, during, and/or after a call, and number of and time points of missed or ignored calls); text messaging (e.g., SMS text messaging) data (e.g., number of messages sent and/or received, message length associated with a contact of the individual, message entry speed, delay between message completion time point and sending time point, message efficiency, message accuracy, time of sent and/or received messages, location of the patient when receiving and/or sending a message); data on textual messages sent through other communication venues (e.g., public and/or private textual messages sent to contacts of the patient through an online social networking system, reviews of products, services, or businesses through an online ranking and/or review service, status updates, "likes" of content provided through an online social networking system, etc.), vocal and textual content (e.g., text and/or voice data that can be used to derive features indicative of negative or positive sentiments, search engine queries, user feedback regarding an application, etc.) and any other suitable type of data. In a variation, collecting a digital communication dataset can include collecting communication data related to patient communications with a health professional (e.g., a nurse, care provider, a pharmacist, a pharmacologist, a health coach, a therapist, a nutritionist, a dietician, an exercise instructor, a personal trainer, etc.). For example, the method 100 can include, facilitating, at an application executing on a patient mobile computing device, communications between patients and health professionals (e.g., health coaches); and collecting a digital communication dataset including information regarding the communications. Additionally or alternatively, receiving a log of use dataset can be performed in any manner analogous to embodiments, variations, and examples of which are described in U.S. application Ser. No. 15/005,923, entitled "Method for Providing Therapy to an Individual" and filed on 25 Jan. 2016, which is herein incorporated in its entirety by this reference.

In relation to receiving the log of use dataset, Block S110 can include accessing the log of use at the mobile communication device of the individual, and transmitting, from the mobile communication device to a computing system, a log of use dataset associated with communication behavior of the individual S112, as shown in FIG. 2. The computing system can be implemented in one or more of a processing module of the mobile communication device, a personal computer, a remote server, a cloud-based computing system, a computing module of any other suitable computing device (e.g., mobile computing device, wearable computing device, etc.), and any other suitable computing module. In transmitting the log of use dataset, a communication module (e.g., a hardware communication module associated with the communication application) can transmit data to the computing system by way of a wired and/or wireless data link (e.g., over Bluetooth, over Bluetooth LTE, etc.).

However, Block S110 can include another other suitable variation of accessing the log of communication, transmitting data from the log of communication, and/or receiving a log of use dataset.

3.2 Passive Data—Receiving a Supplementary Dataset.

As shown in FIGS. 1-2 and 4, Block S120 recites: receiving a supplementary dataset associated with the time period, which functions to unobtrusively receive non-communication-related data from a patient's mobile computing device and/or other device configured to receive contextual data from the patient. Block S120 can include receiving non-communication-related data pertaining to the patient before, during, and/or after (or in the absence of) communication with another individual (e.g., a phone call) and/or computer network (e.g., a social networking application), as described above in relation to Block S110. Block S120 can include receiving one or more of: location information, movement information (e.g., related to physical isolation, related to lethargy), device usage information (e.g., screen usage information related to disturbed sleep, restlessness, and/or interest in mobile device activities), and any other suitable information. In variations, Block S120 can include receiving location information of the patient by way of one or more of: receiving a GPS location of the individual (e.g., from a GPS sensor within the mobile communication device of the patient), estimating the location of the patient through triangulation (e.g., triangulation of local cellular towers in communication with the mobile communication device), identifying a geo-located local Wi-Fi hotspot during a phone call, and in any other suitable manner. In applications, data received in Block S110 and S120 can be processed to track behavior characteristics of the patient, such as mobility, periods of isolation, quality of life (e.g., work-life balance based on time spent at specific locations), and any other location-derived behavior information. In an example, Block S120 can include receiving a mobility behavior supplementary dataset associated with a mobility-related sensor (e.g., single or multi-axis accelerometer, gyroscope, gravity sensor, step counter sensor, step detector sensor, rotation sensor, location sensor, magnetic sensors, pressure sensors, etc.) of the mobile computing device. In a specific example, Block S120 can include receiving a mobility behavior supplementary dataset including linear acceleration data along the x-, y-, and/or z-axis with a multi-axis accelerometer. In another specific example, Block S120 can include receiving a mobility behavior supplementary dataset including rate of rotation data around the x-, y-, and/or z-axis with a multi-axis gyroscope.

Regarding Block S120, a supplementary dataset can additionally or alternatively include data from any suitable patient device, including a cardiovascular device (e.g., cardiovascular therapy device, cardiovascular monitoring device, etc.), a mobile computing device (e.g., a smartphone, a tablet, smart watch, laptop, etc.), a smart appliance (e.g., a smart lighting system, a smart thermometer, a smart oven, a smart media device, etc.), and/or any other suitable patient device. A cardiovascular therapy device can include one or more of: a defibrillator (e.g., an implantable cardioverter defibrillator, automated external defibrillator, etc.), pacemakers, prosthetic heart valves, stents, ventricular assist devices, cardiac ablation catheters, cardiac angioplasty devices, exercise device, and/or other suitable device for provisioning cardiovascular therapy. A cardiovascular monitoring device can include one or more of: a cardiac loop recorder (e.g., for recording heart rhythm), heart rate monitor, blood pressure monitor, hemodynamic monitor, biosignal detector device (e.g., electrooculography, electromyography, electrocardiography, galvanic skin response, magnetoencephalogram, etc.), weight scale (e.g., a smart weight scale), and/or other suitable device for monitoring cardiovascular activity. In a variation, a mobile computing device can perform functions of a cardiovascular device (e.g., a smart watch that includes heart rate monitoring capabilities). In a specific example of the variation, the method 100 can include automatically providing a cardiovascular therapeutic intervention at a cardiac device associated with the patient, where the cardiac device is the mobile computing device. In another example, the method 100 can include automatically providing a cardiovascular therapeutic intervention including initiating provision of medication at a drug delivery cardiac device, where the cardiac device is in communication with the mobile computing device (e.g., over a wireless link). However, Block S120 can include receiving a supplementary dataset associated with any suitable patient device.

As such, data from Blocks S110 and S120 can thus be processed separately and/or can be merged in subsequent blocks of the method 100 to track the patient's mobility during a communication, for instance, in the analysis of Block S140. In variations, Block S120 can additionally or alternatively include receiving mobile usage data, including data indicative of screen unlocks and mobile application usage (e.g., by retrieving usage information from mobile operating system logs, by retrieving usage information from a task manager on a mobile communication device, etc.). Blocks S120 and/or S110 can therefore facilitate tracking of variations and periods of activity/inactivity for a patient through automatically collected data (e.g., from the patient's mobile communication device), in order to enable identification of periods of activity and inactivity by the patient (e.g., extended periods when the individual was hyperactive on the device or not asleep).

In additional variations, Block S120 can additionally or alternatively include receiving one or more of: physical activity- or physical action-related data (e.g., accelerometer data, gyroscope data, data from an M7 or M8 chip, Apple HealthKit data, etc.) of the patient, local environmental data (e.g., climate data, temperature data, light parameter data, etc.), nutrition or diet-related data (e.g., data from food establishment check-ins, data from spectrophotometric analysis, etc.) of the patient, biometric data (e.g., data recorded through sensors within the patient's mobile communication device, data recorded through a wearable or other peripheral device in communication with the patient's mobile communication device) of the patient, and any other suitable data. In examples, one or more of: a blood pressure sensor, and a pulse-oximeter sensor, and an activity tracker can transmit the individual's blood pressure, blood oxygen level, and exercise behavior to a mobile communication device of the individual and/or a processing subsystem implementing portions of the method 100, and Block S120 can include receiving this data to further augment analyses performed in Block S140.

In relation to Block S120, a supplemental dataset is preferably associated with a temporal indicator. For example, Block S120 can include receiving a supplementary dataset (e.g., a mobility behavior supplementary dataset) corresponding to a time period. In a variation, Block S120 can include receiving a supplementary dataset corresponding to a time period in which a cardiovascular treatment (e.g., a cardiovascular therapeutic intervention promoted in Block S160) was administered. For example, Block S120 can include receiving a supplementary dataset collected at a cardiovascular device, the supplementary dataset corresponding to a time period immediately following administration of the cardiovascular treatment. However, a supplemental dataset can be associated with any suitable temporal indicators, or can be distinct from temporal indicators.

In relation to receiving data, Blocks S120 and/or S110 can additionally or alternatively include receiving data pertaining to individuals in contact with the patient during the period of time. As such, Blocks S120 and/or S110 can provide a holistic view that aggregates communication behavior data and contextual data of two sides of a communication involving a patient who is suffering from and/or at-risk of cardiovascular disease. In examples, such data can include one or more of: a second party's location during a phone call with the patient, the second party's phone number, the second party's length of acquaintance with the patient, and the second party's relationship to the patient (e.g., top contact, spouse, family member, friend, coworker, business associate, etc.).

Similar to Block S110, In relation to receiving the supplementary dataset, Block S120 can include transmitting the supplementary dataset from the mobile communication device S122 and/or any other suitable device or system that serves as a source of supplementary data, to the computing system, as shown in FIG. 2. In transmitting the supplementary dataset, one or more sensor modules (e.g., sensor module of the mobile communication device, sensor module of a wearable computing device, sensor of a biometric monitoring device, etc.) can transmit data to the computing system by way of a wired and/or wireless data link (e.g., over Bluetooth, over Bluetooth LTE, etc.). However, Block S120 can include any other suitable variation of transmitting supplementary data, and/or receiving supplementary data.

3.3 Active Data—Receiving a Survey Dataset.

As shown in FIGS. 1-2 and 4, Block S125 recites: generating a survey dataset from a patient response to at least one of a cardiovascular evaluation survey and a psychological evaluation survey. Block S125 thus functions to receive active data provided by surveying the patient, which can enable determination of a cardiovascular health state of the patient. Block S125 is preferably implemented at a module of the computing system described in relation to Block S110 above, but can additionally or alternatively be implemented at any other suitable system configured to receive survey data from one or more patients. The survey dataset (e.g., patient can include interview and/or self-reported information from the patient. Furthermore, the survey dataset preferably includes quantitative data, but can additionally or alternatively include qualitative data pertaining to a cardiovascular state of the patient corresponding to at least a subset of the set of time points (e.g., a time period). The survey dataset preferably includes one or more patient responses to a cardiovascular evaluation survey. In a specific example, the method 100 can include presenting a cardiovascular evaluation digital survey to the patient at the mobile computing device; and generating a survey dataset from a patient response to the cardiovascular evaluation digital survey. A cardiovascular evaluation survey can evaluate one or more of: current medical status (e.g., current medications, symptoms such as fatigue, dizziness, shortness of breath, energy levels, etc.), medical history (e.g., previous appointments, historic cardiovascular health metrics, family history, treatment history, etc.), psychological status (e.g., how the user is emotionally dealing with cardiovascular disease, mood, emotions, etc.), habits (e.g., cardiovascular health monitoring habits, dietary habits, smoking habits, fitness habits, etc.), demographic information (e.g., gender, age, weight, ethnicity, etc.), patient knowledge (e.g., knowledge regarding cardiovascular disease, symptoms, treatments, etc.), risk factors (e.g., factors from cardiac risk indexes such as the Goldman Risk index, Eagle's Cardiac Risk Index, Detsky's Cardiac Risk Index, Lee's Revised Cardiac Risk Index, ACC/AHA Cardiac Risk Classification, etc.) and/or any other suitable information.

In an example of Block S125, the survey dataset can include a patient response to questions inquiring about risk factors described in the Revised Cardiac Risk Index. In particular, Block S125 can include presenting a cardiovascular evaluation survey asking whether patient has a history of ischemic heart disease, a history of congestive heart failure, a history of cerebrovascular disease, history of diabetes requiring preoperative insulin use, chronic kidney disease, and/or whether the patient is undergoing suprainguinal vascular, intraperitoneal, or intrathoracic surgery. Patient responses confirming any of the risk factors in the Revised Cardiac Risk Index and/or other cardiac risk indexes can be used in determining one or more cardiovascular health metrics S130. However, surveys can inquire about any suitable information.

Regarding Block S125, furthermore, while portions of the survey dataset preferably correspond to one or more time windows within the time period of Block S110, portions of the survey dataset can alternatively correspond to any temporal indicator (e.g., time point, time window, time period, etc.) outside of the time period of Block S110 (e.g., as in a pre-screening or a post-screening survey). Additionally or alternatively, Block S125 can include receiving clinical data (e.g., information gathered in a clinic or laboratory setting by a clinician).

In Block S125, the set of time points can include uniformly or non-uniformly-spaced time points, and can be constrained within or extend beyond the time period of the log of use of the native communication application of Block S110. As such, in variations, the set of time points can include regularly-spaced time points (e.g., time points spaced apart by an hour, by a day, by a week, by a month, etc.) with a suitable resolution for enabling detection of changes in a cardiovascular state of the patient. Additionally or alternatively, provision of a survey and/or reception of responses to a survey can be triggered upon detection of an event of the patient (e.g., based upon data from sensors associated with the patient, based upon an output of an analysis of Block S140, etc.) or any other suitable change in cardiovascular state of the patient. For example, Block S125 can include providing a survey and/or generating a survey dataset from a patient response to the survey, based on a cardiovascular treatment regimen (e.g., at a time period immediately following a patient-scheduled time for consuming a cardiovascular medication), digital communication activity (e.g., when the patient displays idle mobile computing device activity, when the user displays active mobile computing device activity, etc.), physical activity level (e.g., when the patient is stationary, when the patient is awake, etc.), and/or any other suitable criteria. Furthermore, for all time points of the set of time points, an identical subset of the set of cardiovascular evaluation surveys can be provided to the patient; however, in alternative variations, different subsets of the set of cardiovascular evaluation surveys can be provided to the patient at different time points of the set of time points. In a variation, Block S125 includes presenting a digital survey at a regular time interval (e.g., every hour, day, week, month, etc.) to the patient at a patient device (e.g., mobile computing device). In another variation, Block S125 can include, at a time period subsequent to cardiovascular treatment administration: providing a survey and/or generating a survey dataset including a patient response to a survey presented during the time period. In a specific example, the method 100 can include promoting a telemedicine communication between the patient and a care provider; and after completion of the telemedicine communication, presenting a digital survey (e.g., a cardiovascular evaluation survey assessing cardiovascular symptoms following the telemedicine communication; a psychological evaluation survey assessing the patient's feelings about the communication, etc.). However, providing a survey and/or generating a survey dataset can be performed at any suitable time.

In relation to Block S125, additionally or alternatively, survey dataset can include survey responses to one or more of: a demographic survey that receives demographic information of the patient; a medication adherence survey (for patients taking medication for a cardiovascular condition); a mood survey; and a social contact survey (e.g., covering questions regarding aspects of the patient's contact with others). However, the set of surveys can include any other suitable surveys configured to assess cardiovascular states of the patient, or adaptations thereof. As such, the survey dataset can include quantitative scores of the patient for one or more subsets of surveys for each of the set of time points (or a subset of the set of time points).

In a variation, Block S125 can additionally include generating a survey dataset from a patient response to a psychological evaluation survey. A psychological evaluation survey can evaluate one or more of: psychosis, depression, bipolar disorder, anxiety, schizophrenia, and/or any suitable mental condition (e.g., a condition described in the Diagnostic and Statistical Manual of Mental Disorders). Additionally or alternatively, Block S125 can include any elements described in U.S. application Ser. No. 14/839,232 entitled "Method for modeling Behavior and Psychotic Disorders" and filed 1 Oct. 2015, U.S. application Ser. No. 14/839,053 entitled "Method for Modeling Behavior and Depression State" and filed 28 Aug. 2015, both of which are herein incorporated in their entireties by this reference. However, a survey dataset can include any suitable information regarding patient responses to any suitable survey.

In some variations, Block S125 can further include facilitating automatic provision of a digital survey (e.g., a digital cardiovascular evaluation survey, a digital psychological evaluation survey, etc.) at the mobile computing device(s) of the patient(s). As such, responses to one or more surveys can be provided by user input at an electronic device (e.g., a mobile computing device of the patient), or automatically detected from user activity (e.g., using suitable sensors). Additionally or alternatively, provision of at least one survey can be performed manually by an entity associated with a patient or received as derived from clinical data, with data generated from the survey(s) received in Block S120 by manual input. Additionally or alternatively, provision of at least one survey and/or reception of responses to the survey can be guided by way of an application executing at a device (e.g., mobile device, tablet) of a caretaker of the patient and/or the patient, wherein the application provides instruction (e.g., in an audio format, in a graphic format, in a text-based format, etc.) for providing the survey or the responses to the survey. Block S125 can, however, be implemented in any other suitable manner (e.g., by verbal communication over the phone, by verbal communication face-to-face, etc.). In a variation, Block S125 can include presenting a digital survey in the form of a multimedia game. In an example, Block S125 can include presenting a set of images representing activities of varying physical vigor (e.g., sleeping, exercising, sitting, standing, etc.) to the patient at a mobile computing device; prompting the patient to select the patient's favorite activities; and generating a survey dataset including the patient's selection of activities. However, a survey can be represented in any suitable form.

Similar to Block S110, In relation to receiving the survey dataset, Block S125 can include transmitting the survey dataset from the mobile communication device S126 and/or any other suitable device or system that serves as a source of survey data, to the computing system, as shown in FIG. 2. In transmitting the survey dataset, one or more data storage modules (e.g., memory module of the mobile communication device, etc.) can transmit data to the computing system by way of a wired and/or wireless data link (e.g., over Bluetooth, over Bluetooth LTE, etc.). However, Block S130 can include another other suitable variation of transmitting survey data, and/or receiving survey data.

Blocks S110, S120, and S125 can thus provide passive data (e.g., unobtrusively collected data) and active data (e.g., survey data) that can be taken as inputs in Block S130 to generate analyses pertaining to present, past, and/or future cardiovascular states of a patient.

Some variations of the method 100 can, however, omit collection of a survey dataset, such that analyses generated in subsequent blocks of the method 100 rely upon the log of use dataset and/or the supplementary dataset in enabling determination of a cardiovascular state of the patient. Thus, analyses of the cardiovascular health of the patient and/or predictive models generated in subsequent blocks of the method 100 can omit use of active data in determining states of the patient and providing appropriate therapies to the patient. Alternatively, variations of the method 100 can omit collection of one or more of the log of use dataset and the supplementary dataset, such that analyses generated in subsequent blocks of the method 100 rely upon the survey dataset in enabling determination of a cardiovascular state of the patient. Thus, analysis of the cardiovascular states of the patient and/or predictive models generated in subsequent blocks of the method 100 can omit use of portions of the datasets described in Blocks S110, S120, and S125 in determining states of the patient and providing appropriate therapies to the patient. Variations of the method 100 can additionally or alternatively include omission or collection of any other suitable type of data for use in subsequent blocks of the method 100.

3.4 Extracting a Cardiovascular Health Metric

As shown in FIGS. 1-4, Block S130 recites: extracting a cardiovascular health metric from at least one of an output of the cardiovascular health predictive model, the log of use dataset, the supplementary dataset, and the survey dataset. Block S130 functions to determine values of one or more cardiovascular health metrics in association with at least one time period. Block S130 can additionally or alternatively include generating a predictive model S140. Block S130 thus enables assessment of a past or current cardiovascular of the patient and/or predicts risk that the patient will trend toward a different (e.g., worsened, improved, etc.) cardiovascular state at a future time point.

Regarding Block S130, the cardiovascular health metric preferably indicates the cardiovascular health of the patient during the time period, but can indicate cardiovascular health of any suitable individual during any suitable time. Additionally or alternatively, the cardiovascular health can include any one or more of a: blood pressure metric (e.g., instantaneous blood pressure, blood pressure variability, etc.), measures indicative of atherosclerosis or other cardiovascular disease, heartbeat metric (e.g., instantaneous heart rate, heart rate variability, average heart rate, resting heart rate, heartbeat signature, etc.), pulse rate metric (e.g., instantaneous pulse rate, pulse rate variability, etc.), physical activity metric (e.g., motion metrics, fitness metrics, etc.), metrics correlated with cardiovascular health (e.g., sleep metrics, etc.), vital signs, pulse oximetry metric, measures of blood vessel stiffness, respiration metric (e.g., respiratory rate, respiratory patterns, etc.), and/or any other suitable metric relating to cardiovascular health.

In relation to Block S130, the cardiovascular health metric is preferably associated with a time period associated with the data (e.g., log of use dataset, supplementary dataset, survey dataset, etc.) from which the metric is generated. Additionally or alternatively, the cardiovascular health metric can be associated with and/or correspond to any suitable temporal indicator.

For Block S130, extracting a cardiovascular health metric is preferably from at least the log of use dataset. For example, Block S130 can include determining a set of digital communication behavior features (e.g., phone calling features, text messaging features, social media features, etc.) from a log of use dataset; and generating cardiovascular health metric from the digital communication behavior features.

In a variation, Block S130 can include generating a cardiovascular health metric based on a log of use dataset describing the content of at least one digital communication involving the patient. Content correlated with cardiovascular health metrics can include content describing one or more of: physical activity (e.g., planned physical activities, lack of planned physical activities, physical vigor associated with discussed physical activities, etc.), fitness level (e.g., diet, restaurant reservations, check-ins, healthiness of restaurants, eating plans, exercise plans, etc.), physiological status (e.g., presence of symptoms associated with cardiovascular disease, energy levels, metabolic function, etc.), psychological status (e.g., mood, emotions, presence of symptoms associated with mental conditions, etc.), and/or any other suitable content. In an example, a set of digital communications describing a series of jogging exercises can be correlated with a decreased risk of cardiovascular disease. In another example, a series of text messages describing frequent restaurant reservations can be correlated with a cardiovascular health metric indicating higher blood pressure. In another example, e-mail message content describing cardiovascular disease symptoms (e.g., shortness of breath, chest pressure, etc.) can be modeled as increasing the probability of cardiovascular disease. However, extracting a cardiovascular health metric based on digital communication content can be performed in any manner.

Additionally or alternatively, in another variation, Block S130 can include generating a cardiovascular health metric based on a log of use dataset describing the participants of at least one digital communication involving the patient.

Participants can include a health professional, an exercise partner (e.g., a sports team member, running partner, etc.), friends, family, strangers, and/or any suitable individual. In an example, frequent communications with an exercise partner can be correlated with an improved cardiovascular health metric. However, log of use data describing participants in a digital communication can be leveraged in any suitable manner for generating a cardiovascular health metric.

Additionally or alternatively, in another variation, Block S130 can include extracting a cardiovascular health metric from a log of use dataset indicating one or more temporal features associated with the log of use dataset (e.g., a temporal indicator describing when one or more digital communications transpired). Temporal features can include frequency of digital communications, timestamp associated with a digital communication (e.g., whether the digital communication was during the day, during the night, on which days did the digital communication transpire, etc.), temporal variability in digital communication (e.g., a high number of digital communications in a first week, and a low number of digital communications in a second week). In an example, generating a cardiovascular health metric can be based on a positive correlation between cardiovascular health and frequency of digital communications. In another example, determining a cardiovascular health metric can be based on a negative correlation between cardiovascular health and temporal variability in digital communications. However, temporal features associated with digital communication behavior of the patient can be used in any suitable manner for generating a cardiovascular health metric.

Relating to Block S130, extracting a cardiovascular health metric can additionally or alternatively be from a supplementary dataset (e.g., received in Block S120), a survey dataset (e.g., received in Block S125), and/or an output of a cardiovascular health predictive model (e.g., generated in Block S140).

As such, in a variation of Block S130, generating a cardiovascular health metric can additionally or alternatively be based on a survey dataset derived from a patient response to a cardiovascular evaluation survey. For example, patient responses to lifestyle habits (e.g., smoking, exercise, diet, etc.) can be used in evaluating cardiovascular risk in generating a cardiovascular health metric. In another example where the risk factors for the Revised Cardiac Risk Index are presented, the number of confirmed risk factors can be translated to a probability of cardiac death, nonfatal myocardial infarction, and nonfatal cardiac arrest. In a specific example, a 0.4% chance of such cardiac incidents can be inferred from 0 confirmed risk factors, 0.9% chance for 1 confirmed risk factor, 6.6% chance for 2 confirmed risk factors, greater than 11% chance for more than 3 confirmed risk factors. However, survey data can be used in any suitable manner for determining one or more cardiovascular health metrics.

In another variation of Block S130, generating a cardiovascular health metric can be based on a mobility behavior supplementary dataset. For example, physical activity level can be inferred from motion sensor data (e.g., steps taken, distance traveled, etc.), location data (e.g., GPS tracking, etc.), and/or other suitable mobility behavior data. The physical activity level can have a positive correlation with cardiovascular health. In another example, GPS data indicating travel to multiple international geographic locations in a short period of time, combined with a low frequency of digital communications, can indicate a higher risk of deterioration of cardiovascular health. In a specific example, the method 100 can include receiving a patient mobility behavior supplementary dataset including a travel metric indicating a distance traveled by the patient during the time period, where the patient mobility behavior supplementary dataset corresponds to the time period (e.g., a time period associated with a received log of use dataset), and where generating the cardiovascular health metric includes generating the cardiovascular health metric from at least one of the patient mobility behavior supplementary dataset and digital communication behavior features (e.g., determined based on a received log of use dataset). However, using mobility behavior data to determine cardiovascular health can be performed in any suitable manner.

In another variation of Block S130, determining a cardiovascular health metric can be derived from a cardiovascular device supplementary dataset. For example, the method 100 can include receiving a heart rate supplementary dataset collected at a heart rate sensor of a cardiovascular device, wherein the heart rate supplementary dataset corresponds to the time period (e.g., a time period in which a log of use dataset was collected), wherein generating the cardiovascular health metric includes generating the cardiovascular health metric from the digital communication behavior features and the heart rate supplementary dataset. In another example, adherence behaviors (e.g., with respect to cardiovascular medication) inferred from automatic medication dispenser data can be compared against adherence behaviors inferred from patient responses to cardiovascular evaluation surveys, in order to determine a user adherence to a treatment regimen influencing cardiovascular health. In another example, an electrocardiography (ECG) supplementary dataset can be augmented with a digital communication dataset in order to determine user digital communication behaviors corresponding to time periods of ECG readings indicating poor cardiovascular health. In a specific example, ECG readings indicating a high heart rate and/or irregular heart rhythm can be associated with time periods in which digital communications transpired between the patient and a particular individual (e.g., a particular family member). Such correlations can be used in models for determining a cardiovascular health metric (e.g., when a log of use dataset indicates a plurality of digital communications with the particular individual) and/or determining a cardiovascular health intervention (e.g., cautioning the user to initiate digital communication with the particular individual). In another example, digital communication content data indicating a dietary habit can by combined with a weight scale supplementary dataset in evaluating the contribution of the dietary habit to cardiovascular health. However, a cardiovascular device supplementary dataset (e.g., fitness monitor data, smart appliance data such as a smart oven, etc.) can be used in any manner for generating a cardiovascular health metric.

In another variation of Block S130, determining a cardiovascular health metric can be based on an event-related supplementary dataset. Event data can be collected from a calendar application, a reminder application, a social network application, a purchase history, and/or any suitable source. For example, event data collected from a calendar application can be parsed to determine the level of physical activity involved with a particular type of event (e.g., a social party, eating out at a restaurant, exercise, etc.), which can be mapped to contribution to cardiovascular health. In another example, event data indicating user-created reminders for attending health professional appointments, adhering to treatment regimens, and/or other suitable indicators of treating cardiovascular issues can be used as a proxy for treatment adherence and/or whether the user is actively taking action to prevent cardiovascular degradation. In another example, purchase histories (e.g., of exercise equipment, food, alcohol, fitness book, self-improvement guides, etc.) can be analyzed for evaluating user lifestyle and contribution to cardiovascular health. However, event-related data can be used in any manner for determining a cardiovascular health metric.

In another variation of Block S130, generating a cardiovascular health metric can be derived from a media supplementary dataset. Media data types can include image data, video data, audio data, and/or any suitable media data. Media data can include temporal data (e.g., media duration, media timestamps, etc.), content data, and/or any suitable data related to the media. For example, a set of photos captured by the user during a time period can be analyzed to determine the scenes (e.g., nature, inside a building, outside a building, daytime, nighttime, etc.) in which the photos were taken. The presence or frequency of particular scene types can be correlated with cardiovascular health. In a specific example, a high proportion of nature photographs can indicate a calming experience involving physical activity, and consequently can be correlated with an improvement in cardiovascular health. However, media data can be used in any manner for determining a cardiovascular health metric.

Relating to Block S130, one or more cardiovascular health metrics can be in the form of verbal (e.g., high risk of cardiovascular disease), numerical (e.g., probability of myocardial infarction, cardiovascular risk scale from 1-10, etc.), graphical, audio, and/or other suitable format of information.

Block S130 preferably includes determining one or more cardiovascular health metrics using a cardiovascular health predictive model. Cardiovascular health predictive models can incorporate probabilistic properties, heuristic properties, deterministic properties, and/or any other suitable properties for generating a cardiovascular health metric. In a variation, generating a cardiovascular health metric includes generating a cardiovascular health machine learning model (e.g., as further described in Block S140). In another variation, generating a cardiovascular health metric includes generating a decision tree model with internal nodes and branches selected based on correlations between cardiovascular health and digital communication behavior, supplementary data, and/or survey data, where generating the cardiovascular health metric is based on the correlations. In another variation, determining the cardiovascular health metric can include generating a patient profile from at least one of the log of use dataset, supplementary dataset, and survey dataset; comparing the patient profile to a reference profile associated with one or more reference cardiovascular health metrics; and determining the cardiovascular health metric based on the comparison and the reference cardiovascular health metrics. Reference profiles can include digital communication behavior profiles of patients with known cardiovascular conditions, composite patient profiles, manually curated patient profiles, automatically generated patient profiles, and/or any suitable reference patient profile. In another variation, Block S130 can include augmenting a cardiovascular device supplementary dataset with one or more cardiovascular health metrics. In this variation, the cardiovascular device supplementary dataset and the cardiovascular health metrics preferably correspond to a same time period or respectively correspond to overlapping time periods. For example, blood pressure readings during a time period from a blood pressure monitor can be augmented with cardiovascular health metric insights determined from log of use data during the time period (e.g., a time period of high blood pressure corresponded with a high frequency of digital communications, which can educate a user about their physiological responses associated with certain digital communication behaviors). However, any suitable approach can be leveraged in generating a cardiovascular health metric.

Figure 8:
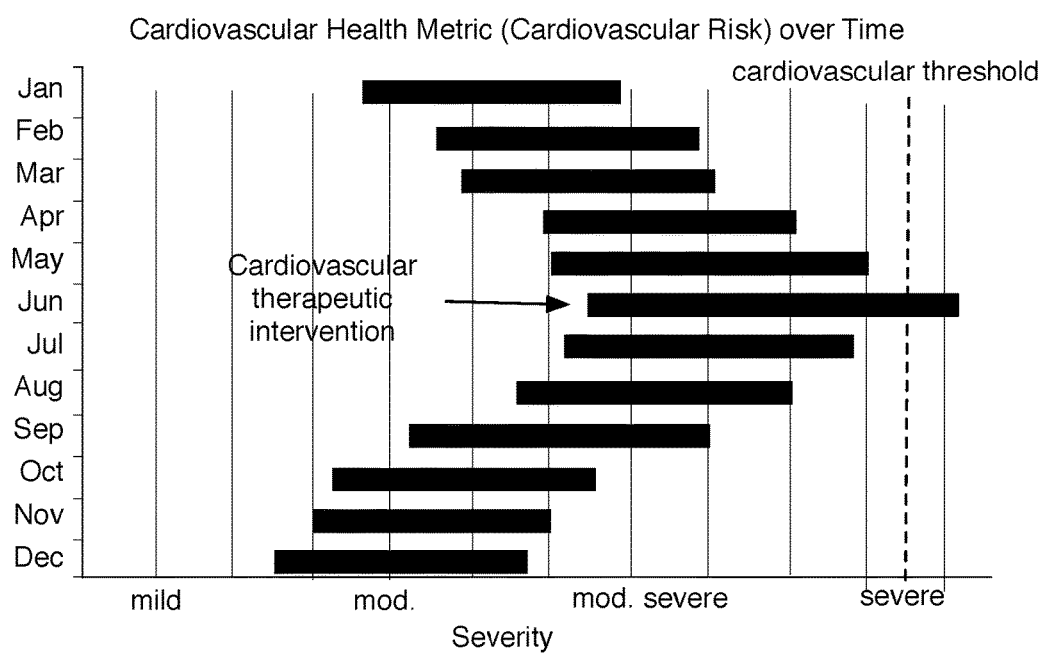
FIG. 8 is a graphical representation of cardiovascular health metrics over time.

Regarding Block S130, extracting a cardiovascular health metric can be performed automatically at specified time intervals (e.g., every hour, day, week, etc.), in response to satisfaction of a condition (e.g., a user request for a cardiovascular evaluation, a log of use dataset indicating abnormal digital communication behavior, a supplementary dataset indicating irregular mobility behavior, a survey dataset indicating poor dietary habits, etc.), and/or performed at any suitable time. In a variation, Block S130 can be performed in response to satisfaction of a data collection threshold. For example, generating a cardiovascular health metric can be performed when collected data exceeds an amount of data threshold, a type of data threshold, etc. In a specific example, data thresholds can be set based on an amount of data required for generating a cardiovascular risk metric with high confidence. In another variation, generating a cardiovascular health metric can be performed at any suitable time before, during, and/or after a patient's healthcare experience (e.g. prior to initial healthcare visit, during a visit, subsequent to visits). For example, as shown in FIG. 8, cardiovascular health metrics can be used to monitor patient treatment response to a cardiovascular medication. In a specific example, the method 100 can include collecting a log of used dataset, supplementary dataset, and/or survey dataset during a time period subsequent to patient consumption of a cardiovascular medication, and wherein generating the cardiovascular health metric includes generating a treatment response metric indicating treatment response to the cardiovascular medication during the time period. In another variation, Block S130 can include generating cardiovascular health metrics describing the probability of recurrence of cardiovascular symptoms (e.g., shortness of breath, fatigue, dizziness, etc.) and/or cardiovascular incidents (e.g., myocardial infarction, etc.), based on continuous collection and processing of log of use data, supplementary data, and/or survey data. However, Block S130 can be performed at any suitable time.

Block S130 is preferably fully or substantially performed at a remote server. Additionally or alternatively, portions of Block S130 can be performed at a patient device, a third party (e.g., health professional) device, and/or at any suitable component.

However, extracting a cardiovascular health metric can be performed in any manner.

3.4.A Cardiovascular Health Metric—Predictive Model

As shown in FIGS. 1-2 and 4, extracting a cardiovascular health metric can optionally include generating a cardiovascular health predictive model S140, which functions to leverage one or more predictive models with one or more datasets of the method 100 in generating one or more cardiovascular health metrics.

Regarding Block S140, a cardiovascular health predictive model preferably uses one or more machine learning techniques and training data (e.g., from the patient, from a population of patients), data mining, and/or statistical approaches to generate more accurate models pertaining to the patient's cardiovascular states (e.g., over time, with aggregation of more data). For example, Block S140 can include generating a cardiovascular health predictive model based upon a log of use dataset and a mobility behavior supplementary dataset. Training data can be labeled with cardiovascular disease risk classification (e.g., high risk, at-risk, optimal risk, etc.), values of a cardiovascular health metric, risk factors (e.g., from a cardiac risk index), fitness level, recommended therapeutic intervention (e.g., therapeutic interventions with positive treatment responses for certain reference profiles), and/or any other suitable label related to cardiovascular health. As such, Block S130 is preferably implemented at a computing system configured to process data from one or more of the log of use dataset, the supplementary dataset, and the survey dataset. The computing system can be the same computing system associated with one or more of Blocks S110-S130 of the method 100, or can alternatively be any other suitable computing system.

In generating the predictive model, Block S140 preferably uses input data including one or more of: communication behavior data from the log of use dataset, data from supplementary dataset, and data from the survey dataset to provide a set of feature vectors corresponding to time points of the time period. For example, Block S140 can include determining digital communication behavior features based on a log of use dataset. Feature selection approaches (e.g., for selecting digital communication behavior features) can include one or more of: factor analysis approaches that implement statistical methods to describe variability among observed features in terms of unobserved factors, in order to determine which features explain a high percentage of variation in data; correlation feature selection (CFS) methods, consistency methods, relief methods, information gain methods, symmetrical uncertainty methods, and any other suitable methods of feature selection. In variations, feature selection approaches can be implemented for any passive data (e.g., communication data, mobility-related data, activity-related data, biometric parameter-related data, etc.), wherein a linking analysis of Block S130 is then used to determine associations between features of passive data and states of cardiovascular disease determined from active data (e.g., of the survey dataset). Analysis of the passive data in relation to the active data, with regard to feature selection and associations between passive and active data can, however, be performed in any other suitable manner.

In one variation of Block S140, the feature vectors can include features (e.g., digital communication behavior features) related to aggregate communication behavior, interaction diversity, mobility behavior (e.g., mobility radius as a measure of distance traveled by the patient within a given time period, such as the weekend), a number of missed calls, and a duration of time spent in a certain location (e.g., at home). In examples, feature vectors can be generated based upon aggregation of phone, text message, email, social networking, and/or other patient communication data for a particular period of time into one or more features for the patient for the particular time period. Furthermore, a feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). Additionally, combinations of features can be used in a feature vector. For example, one feature can include a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the patient's mobile computing device. Feature vectors can additionally or alternatively include features based on analysis of voice communications, textual communications, mobile application activity usage, location data, and any other suitable data which can be based on variance, entropy, or other mathematical and probabilistic computations of basic data (e.g., a composite activity score, a composite socialization score, a work-life balance score, a quality-of-life score). However, the feature vectors can be determined in any other suitable manner.

In some variations, Block S140 can additionally or alternatively include deriving features (e.g., digital communication behavior features) based upon one or more of: audio data and visual data of the patient (e.g., during communication, at one or more time points of the set of time points), in order to include additional inputs into a risk model for determination of a cardiovascular health metric. In one variation, processing of audio data from the patient can be used to determine aspects of the voice and/or mood of a patient, in order generate feature vectors, incorporating voice-related parameters (e.g., pitch, volume, speed of speech, modulation of speech, differences in voice-related parameters for different contacts, etc.) that can be used to detect changes in the cardiovascular state of a patient that are indicative of changes in cardiovascular health metrics. Additionally or alternatively, processing of visual data (e.g., images, video) of the patient can be used to aspects of the facial expressions, body language, and/or mood of a patient, in order generate feature vectors, incorporating facial expression- and/or body language-related parameters (e.g., eyebrow position, pupil dilation, expressions indicative of positive mood, expressions indicative of negative mood, stance, speed of movement, etc.) that can be used to detect changes in the cardiovascular health. As such, feature vectors processed by a predictive model in Block S140 can include elements derived from audio and/or visual data, in order to characterize or anticipate changes in a patient's cardiovascular. In specific examples, such features can even be used to classify or diagnose patients with specific types of cardiovascular disease and/or cardiovascular disease risk levels.

In some variations, Block S140 can include utilizing statistics-based feature selection approaches to determine a subset of features from the log of use dataset, the supplementary dataset, and/or the survey dataset that have a high predictive power and/or high accuracy in generating one or more outputs of the predictive model. In examples, the statistical approaches can implement one or more of: correlation-based feature selection (CFS), minimum redundancy maximum relevance (mRMR), Relief-F, symmetrical uncertainty, information gain, decision tree analysis (alternating decision tree analysis, best-first decision tree analysis, decision stump tree analysis, functional tree analysis, C4.5 decision tree analysis, repeated incremental pruning analysis, logistic alternating decision tree analysis, logistic model tree analysis, nearest neighbor generalized exemplar analysis, association analysis, divide-and-conquer analysis, random tree analysis, decision-regression tree analysis with reduced error pruning, ripple down rule analysis, classification and regression tree analysis) to reduce questions from provided surveys to a subset of effective questions, and other statistical methods and statistic fitting techniques to select a subset of features having high efficacy from the data collected in Blocks S110, S120, and/or S125. Additionally or alternatively, any assessment of redundancy or efficacy in a feature derived from data of Blocks S110, S120, and/or S125 can be used to provide a measure of confidence in an output of the predictive model from one or more input features. Furthermore, the statistical approach(es) of Block S140 can be used to strategically reduce portions of data collected based upon redundancy and/or lack of utility of the data. Even further, the statistical approaches/feature selection approaches can be used to entirely omit collection of portions of the data (e.g., responses to specific surveys or portions of surveys can render responses to other portions of surveys or other surveys redundant), in order to streamline the data collection in Blocks S110, S120, and/or S125.

In still other examples of Block S140, correlations between active data and passive data can be used to streamline data collection associated with Blocks S110, S120, and/or S125. However, any other suitable data derived from Blocks S110, S120, and S125 can be used to increase efficacy of data collection and/or determination a cardiovascular health metric in Blocks S130 and S140. Additionally or alternatively, any assessment of redundancy or efficacy in a feature derived from data of Blocks S110, S120, and/or S125 can be used to provide a measure of confidence in a cardiovascular health metric determined from the feature(s).

In some embodiments, the predictive model generated in Block S140 can process a set of feature vectors according to methods described in relation to the predictive modeling engine described in U.S. application Ser. No. 14/839,232 entitled "Method for modeling Behavior and Psychotic Disorders" and filed 1 Oct. 2015, U.S. application Ser. No. 14/839,053 entitled "Method for Modeling Behavior and Depression State" and filed 28 Aug. 2015, and U.S. application Ser. No. 13/969,339 entitled "Method for Modeling Behavior and Health Changes" and filed 16 Aug. 2014, each of which are incorporated herein in their entirety by this reference; however, the predictive model can alternatively be generated in any other suitable manner. As such, in variations of the model(s), a set of feature vectors from the input data can be processed according to a machine learning technique (e.g., support vector machine with a training dataset) to generate the value(s) of one or more cardiovascular health metrics in association with a time period. In one example, the predictive model can incorporate historical data from the patient (e.g., survey responses from a prior week, a history of passive data from the log of use, etc.), with more weight placed upon more recent data from Blocks S110-S125 in determination of a cardiovascular health metric associated with a time period; however, the predictive model can be implemented in any other suitable manner.

Furthermore, for Block S140, in extensions of the method 100 to a population of patients, the predictive model can be used to identify differences in passive data and/or active data, as associated with cardiovascular health, between different demographics of individuals. For instance, the predictive model can be used to identify sets of feature vectors and/or subsets of features (e.g., related to communication behavior, related to survey responses, related to mobility behavior, etc.) that have high efficacy in determining risk/severity for one or more of: different genders, different age groups, different employment statuses, different ethnicities, different nationalities, different socioeconomic classes, and any other suitable demographic difference. In a variation, the method 100 can include forming a subgroup of patients based on medical status (e.g., symptoms, cardiovascular diseases, treatments, medication regimens, etc.); generating a cardiovascular health predictive model from training data (e.g., log of use data, supplementary data, survey data, etc.) associated with patients from the subgroup; and extracting a cardiovascular health parameter from an output of the cardiovascular health predictive model. In a specific example, the method 100 can include assigning the patient to a cardiovascular subgroup of a set of cardiovascular subgroups, based on a survey dataset including a patient response to a the cardiovascular evaluation digital survey; and retrieving a subgroup predictive model corresponding to the cardiovascular subgroup, wherein generating the cardiovascular health metric is in response to retrieving the subgroup predictive model, and wherein the cardiovascular health predictive model is the subgroup predictive model. However generating and/or leveraging predictive models for particular populations, subpopulations, and/or subgroups, can be performed in any manner.

Regarding Block S1140, while some variations of machine learning techniques are described above, in relation to generation of the predictive model, Block S140 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

In a variation of Block S140, the cardiovascular health predictive model can include a treatment response model configured to output a cardiovascular health metric describing a patient response to a cardiovascular treatment (e.g., a cardiovascular therapeutic intervention, a cardiovascular medication, a cardiovascular-related procedure, etc.). However, generating and/or using a treatment response model can be performed in any manner.

In another variation, Block S140 can additionally or alternatively include processing datasets associated with Blocks S110, S120, and/or S125 with an adherence model configured to assess and/or predict a state of adherence to a medication regimen (e.g., a cardiovascular medication regimen) by a patient. The adherence model can be an embodiment, variation, or example of an adherence model as described in U.S. application Ser. No. 13/969,339, entitled "Method for Modeling behavior and Health Changes", but can alternatively be any other suitable adherence model.

3.4.B Cardiovascular Health Metric—Threshold Conditions

As shown in FIG. 2, Block S130 can additionally or alternatively include generating an analysis of a cardiovascular health state of the individual, which can include generating comparisons between different threshold conditions (e.g., cardiovascular threshold conditions) and one or more of: components of the log of use dataset, components of the supplementary dataset, components of the survey dataset and predictive model outputs (e.g., cardiovascular health metrics). As such, as shown in FIG. 2, generating the analysis of cardiovascular health state of the individual in Block S130 can include one or more of: generating a first comparison between a first threshold condition and a passive data component derived from one or more of the log of use dataset and the supplementary dataset S131; generating a second comparison between a second threshold condition and an active data component derived from the survey dataset S132; and generating a third comparison between a third threshold condition and an output of the predictive model S133. The comparison(s) generated in Blocks S131-S133 can thus indicate that the value(s) of parameters associated patient cardiovascular health is/are one or: above the associated threshold condition(s), not significantly different from the associated threshold condition(s), and below the associated threshold condition(s) in triggering a notification (e.g., in Block S150), a therapeutic intervention (e.g., in Block S160), and/or any suitable action. Even further, the comparison(s) to the threshold condition(s) can be based upon multiple values of a parameter or different parameters (e.g., parameters of active data, parameters of passive data, parameters from a predictive model, etc.) in combination. In Blocks S131-S133, the threshold condition(s) can be a threshold value of a parameter or a threshold range of values, wherein the threshold range of values is defined by a first limiting value and a second limiting value. Comparison to the threshold condition(s) in Blocks S131-S133 can thus be performed in a manner that is inclusive of a limiting value, or alternatively be performed in a manner that is exclusive of a limiting value.

The comparisons of Blocks S131, S132, and/or S133 can thus be associated with parameters of the cardiovascular state of the individual used to assess cardiovascular health and/or to improve cardiovascular health in blocks of the method 100. Blocks S131, S132, and S133 thus function to process the outputs of Blocks S110, S120, S140, and/or other suitable portions of the method 100, such that the resolution actions of Block S150 and/or Block S160 are derived from at least one of an active component (i.e., a component derived from the survey response dataset), a passive component (e.g., a clinically-informed behavioral rule component determined by heuristics, a supplementary dataset, etc.), and a component derived from a cardiovascular health model. In particular, consideration of the active component, the passive component, and the component derived from the predictive model can significantly strengthen the efficacy of the resolution actions implemented in Block S150 and/or Block S160, as shown in FIG. 2. Furthermore, each of the active component, the passive component, and the predictive model component can have an associated temporal indicator (e.g., time period) that is identical or different to temporal indicators of analysis of the other components. Additionally, analysis of each of the active component, the passive component, and the predictive model component can occur within one or more temporal indicators that are different from the temporal indicator of an associated resolution action.

Block S131 recites: generating a first comparison between a first threshold condition and a passive data component derived from one or more of the log of use dataset and the supplementary dataset. In Block S131, generating the comparison between the first threshold condition and a passive data element can include defining one or more categories of passive behaviors of the individual (e.g., related to lethargy, physical activity, social isolation, diet, physical isolation, evolution of the patient's support network, time spent at work, weekly behavioral patterns, habits, etc.) based upon historical behavior of a patient within a duration of time (e.g., immediately prior 4-6 weeks of the individual's life). Then, Block S131 can include comparing the features of, or evolution in the passive behavior(s) of, the individual to the first threshold condition. In variations wherein the passive behaviors of the patient are monitored for a duration of time, the first threshold condition can additionally or alternatively include a frequency threshold and/or a frequency-within-a-duration-of-time threshold, in relation to generation of an indication based upon a passive data component.

Figure 9:
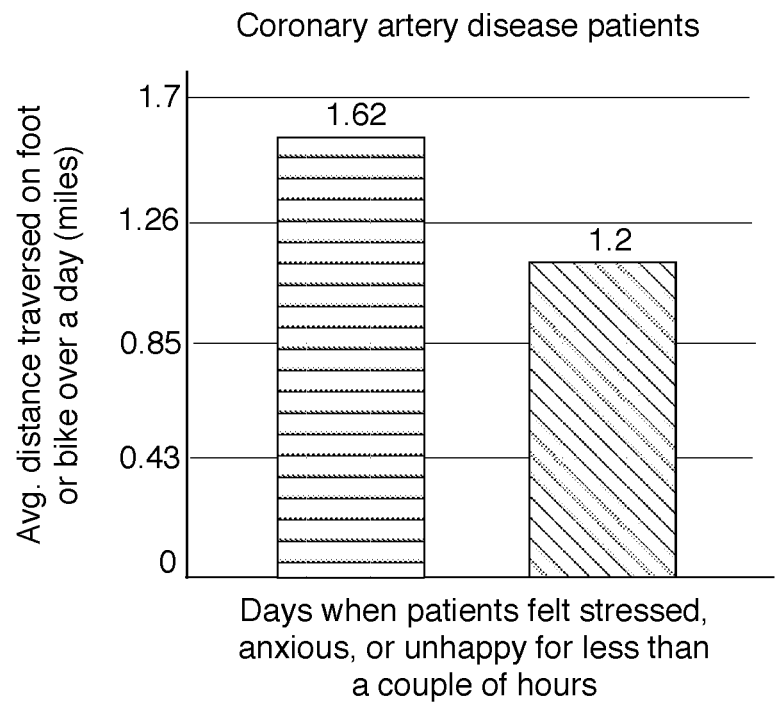
FIGS. 9-11 are graphical representation of correlations between mobility behavior and psychological health for cardiovascular disease patients.
Figure 10:
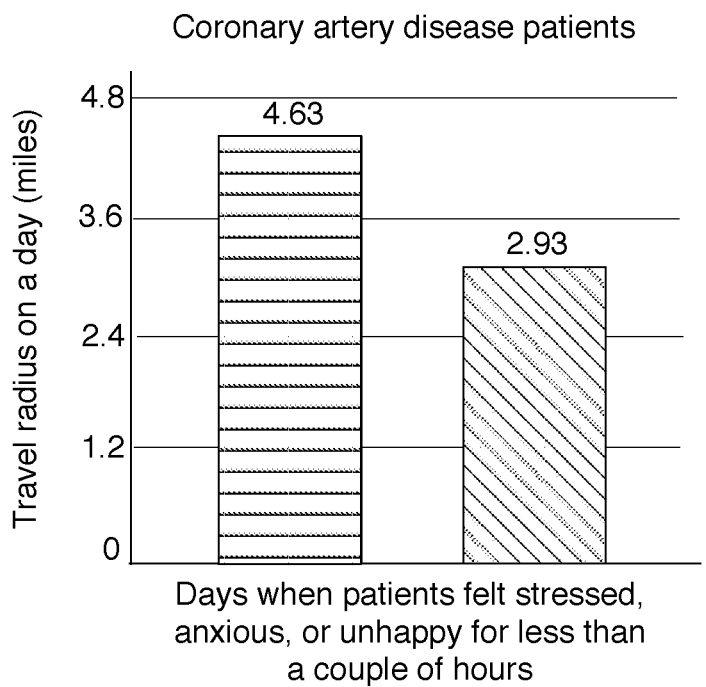
Figure 11:
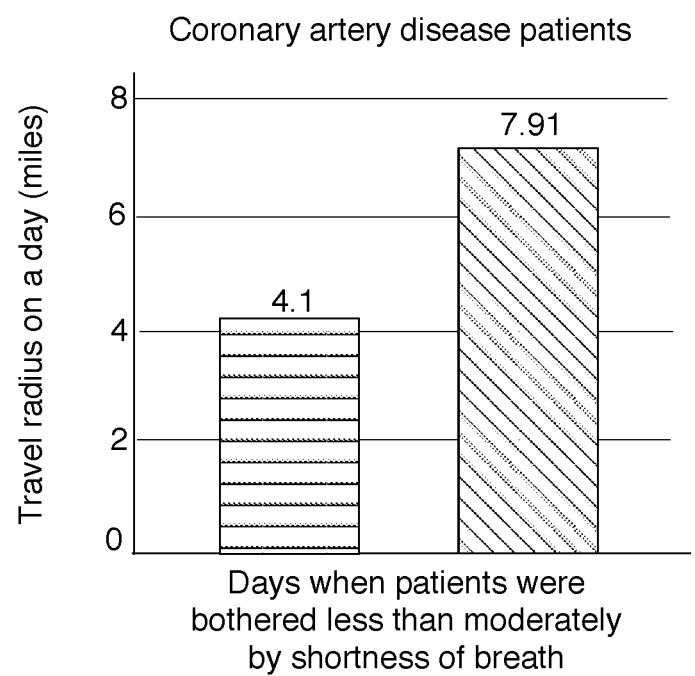

In variations of Block S131, the first threshold condition can include one or more of: a threshold condition of a mobility-related parameter than the $10^{th}$ percentile of values of the mobility-related parameter (e.g., mobility radius) for the time period (e.g., a time window of 30 days, including 15 values of the mobility-related parameter) for the patient; a threshold condition of a mobility less than the $20^{th}$ percentile of values of a mobility-related parameter (e.g., mobility radius) for the time period (e.g., a time window of 30 days, including 15 values of the mobility-related parameter); a threshold condition of a travel radius of less than 3 miles a day (e.g., which can be correlated with increased stress, anxiety, and unhappiness in coronary artery disease patients), as shown in FIG. 10; a threshold condition of an average distance traveled on foot or bike over a day of less than 1.5 miles (e.g., which can be correlated with increased stress, anxiety, and unhappiness, in coronary artery disease patients), as shown in FIG. 9; a threshold condition of travel radius on a day of less than 5 miles (e.g., which can be correlated with less severe shortness of breath), as shown in FIG. 11; a threshold condition of a number of outgoing SMS messages less than 2 messages per day for a period of three consecutive days; a threshold condition of a number of incoming SMS messages less than 2 messages per day for a period of 5 consecutive days; any other suitable threshold condition; and any other suitable combination of threshold conditions.

In examples of Block S131, the first comparison can thus facilitate identification of one or more of: a degree of physical activity (e.g., a time period of high physical activity as indicated by mobility-behavior data indicating a travel radius greater than a threshold condition), a degree of social activity (e.g., a time period with increased stress due to lack of digital communications lasting more than 2 minutes), a degree of treatment adherence (e.g., a time period of high cardiovascular treatment adherence as indicated by user confirmation of reminders regarding consumption of medication), a degree of treatment response (e.g., positive treatment response as indicated by digital communication content describing healthy physical function), and/or any other suitable condition for indication generation correlated with cardiovascular health.

Block S132 recites: generating a second comparison between a second threshold condition and an active data component derived from the survey dataset. In Block S132, generating the second comparison between the second threshold condition and the active component derived from the survey response dataset can include assigning a score to one or more elements of the survey response dataset for a patient (e.g., based upon one instance of survey response provision, based upon multiple instances of survey response provision), and comparing the score(s) to the second threshold condition. For example, for a survey posing "yes" or "no" questions, a score corresponding to the number of "yes" responses by the user can be assigned. In variations wherein the survey response dataset includes responses to survey questions (e.g., a repeat set of survey questions) at each of a set of time points, the second threshold condition can additionally or alternatively include a frequency threshold and/or a frequency-within-a-duration-of-time threshold, in relation to generation of an indication based upon an active component. Furthermore, threshold conditions can be defined in relation to a baseline for each patient, as determined from historical behavior of the patient.

As such, in variations of Block S132, the second comparison can indicate one or more of: a score greater than a given threshold; a score greater than a given threshold for a certain duration of time; a change in score greater than a given threshold; a change in score greater than a given threshold as derived from the patient's historical score data; and any other suitable comparison. Furthermore, the comparison(s) can additionally or alternatively be generated based upon a percentile condition, a standard deviation (e.g., in score) condition, outlier detection analysis (e.g., of a score in relation to scores from the individual), verbal content (e.g., whether a particular word was included in a patient response) and/or any other suitable condition, based upon analysis of a single patient, based upon analysis of a population of patients, and/or any other suitable grouping of patients.

In a specific example of Block S132, a survey dataset can include a score based on the number of risk factors (e.g., smoking, high cholesterol, high blood pressure, previous cardiac surgery, etc.) that a patient has confirmed in the patient response to the survey. Risk factors can be weighted and/or have any suitable contribution to the survey score. The score can be compared to a threshold score, and exceeding the threshold score can initiate provision of a notification (e.g., in Block S150) and/or a therapeutic intervention (e.g., in Block S160

Block S133 recites: generating a third comparison between a third threshold condition and an output of the predictive model. In variations, Block S133 can include comparing one or more cardiovascular health metrics (e.g., risk classification for cardiovascular disease, probability of myocardial infarction, etc.) to one or more threshold cardiovascular health metric values. In Block S133, generating the third comparison between the third threshold condition and the output of the predictive model can include identification of a classification (e.g., a learned, complex, non-intuitive, and/or behavioral association exhibited by the individual), and comparing the classification to a threshold condition. In variations, a single feature and/or combinations of features derived from the log of use dataset, the supplementary dataset, and, the survey response dataset (e.g., with weighting among factors) can be compared to one or more threshold conditions. In variations and examples, the third comparison can be generated as described in U.S. application Ser. No. 13/969,339, entitled "Method for Modeling Behavior and Health Changes" and filed on 16 Aug. 2014.

As such, in one example of Blocks S131, S132, and S133, accounting for a passive component, an active component, and a predictive model component, a determination of a cardiovascular state of the patient can be based upon: a first passive component (e.g., related to communication behavior) generated from behavior analyzed over a first duration of time, a second passive behavioral component (e.g., related to mobility of the individual) generated from behavior analyzed over a second duration of time overlapping with the first duration of time, scoring of a survey, and a predictive model component for third duration of time (e.g., overlapping with the period of the survey), wherein the predictive model component implements an aggregated learning approach based upon multiple individual models (e.g., each assessing different parameters and/or different time periods of patient behavior).

The analyses of Block S130 can, however, include generation of any other suitable comparison and/or any other suitable output which serve as parameters of the cardiovascular health state of the individual. Additionally or alternatively, the comparison(s) generated in Blocks S131, S132, and S133 can include identification or analysis of patient progress through a cardiovascular condition (e.g., in relation to persistence of symptoms, in relation to worsening of symptoms, in relation to improvement of symptoms, etc.).

3.5 Providing a Cardiovascular-Related Notification

Block S150 recites: providing a cardiovascular-related notification, which functions to provide cardiovascular health-related information and/or advice to the patient and/or care provider for improving the cardiovascular health state of the patient.

In relation to Block S150, a cardiovascular-related notification preferably includes cardiovascular health-related information (e.g., generated cardiovascular health metrics, log of use data, supplementary data, survey data, etc.), but can include any suitable information. The notification can be an alert (e.g., push alert), text message (e.g., SMS message), e-mail, telephone call, verbal, graphical, textual, haptic, audio, video, and/or of any suitable format. In an example, Block S150 can include providing a haptic alert to the patient at the cardiovascular device in response to the cardiovascular health metric satisfying a cardiovascular threshold condition (e.g., a condition established in Block S131, S132, and S133). Notifications can be provided to any one or more of: a patient, a health professional, a family member, a friend, and/or any other suitable entity. However, a cardiovascular-related notification can be otherwise configured.

For Block S150, providing a cardiovascular-related notification is preferably based upon a cardiovascular-related parameter associated with at least one of the log of use data, supplementary dataset, survey dataset, and/or an output of a cardiovascular health predictive model (e.g., a cardiovascular health metric). Block S150 can thus include generating a notification upon detection, at the computing system performing the analysis, that one or more outputs (e.g., comparisons) from the analysis of cardiovascular health state satisfy associated threshold conditions (e.g., in Block S131, S132, S133, etc.). The notification of Block S150 can be an alert that prompts transmission of a notification to an entity (e.g., health professional, family member, friend, etc.) associated with the patient, for instance, for therapeutic intervention. The alert can additionally or alternatively include an alert that serves as an input into a subsequent computer-implemented module for automatically providing an intervention to the patient (e.g., in Block S160), the intervention intended to improve the cardiovascular health of the patient.

Furthermore, for Block S150, in relation to an entity associated with the patient(s), the notification(s) can be provided at a dashboard of an electronic interface (e.g., web portal, computing device, etc.) accessible by the entity. In the example shown in FIGS. 5 and 6, notifications can be provided at a dashboard of a web portal. The notification(s) can be text-based alerts including a type of alert (e.g., related to active data, related to passive data), a value of cardiovascular health metric, a graphic that displays values of one or more scores of a survey (e.g., a cardiovascular evaluation survey, a daily mood survey, etc.), and/or any suitable information. In the example, the graphic can include tags that facilitate identification of associations between cardiovascular health and passive data and/or active data. The dashboard can further provide an option to resolve a notification, wherein in examples, resolution of the notification can include any one or more of: initiating a therapeutic intervention (e.g., in Block S160), notifying another entity, storing data, saving data, publishing data, saving data, and/or any suitable action. However, providing a cardiovascular-related notification through an electronic interface dashboard can be performed in any manner.

Relating to Block S150, notifications can be provided with any suitable regular or non-regular frequency, can be provided with a sequence or in a random manner, can be triggered by an event, or can be provided in any other suitable manner. Providing a cardiovascular-related notification is preferably in real-time (e.g., in response to a patient request for cardiovascular health evaluation; during the time period in which a log of use dataset, supplementary dataset, and/or survey dataset is collected, etc.) In a specific example, Block S150 can include, in response to the cardiovascular parameter (e.g., a cardiovascular health metric, a component of a log of use dataset, a supplementary dataset, a survey dataset, etc.) satisfying a cardiovascular health threshold (e.g., in Block S131, S132, S133), providing a cardiovascular-related notification. However, Block S150 can be performed at any suitable time.

In a variation of Block S150, a mobile computing device of a patient can download and subsequently display the notification for the patient at a display of the mobile computing device. The notifications can be personalized to the patient, or can be provided in the same manner to each of a population of patients. For example, notifications tailored to a subgroup of coronary artery disease patients can include language that aids the patients in dealing with symptoms specific to coronary artery disease. In variations wherein the notifications are personalized to the patient, Block S160 can utilize a machine learning technique or any other suitable computational process, as described above, to identify the types of notifications that the patient responds positively to and/or negatively to, as assessed by patient outcomes in relation to cardiovascular health.

In another variation, Block S150 can include generating and/or providing a patient cardiovascular health report to a patient, health professional, and/or other suitable entity. The patient cardiovascular health report preferably describes at least one cardiovascular health-related parameter associated with a passive dataset, active dataset, and/or one or more outputs of a cardiovascular health predictive model. Additionally or alternatively, a patient cardiovascular health report can include a diagnostic analysis (e.g., diagnosing cardiovascular disease or an associated risk level), treatment recommendations, treatment response assessments, and/or any suitable information. However, generating and/or providing a patient cardiovascular health report can be performed in any manner.

In another variation, Block S150 can include updating one or more medical records (e.g., an electronic health records) associated with the patient. Updating one or more medical records preferably includes modifying the medical records to include cardiovascular-health related information derived from one or more blocks of the method 100. However, updating one or more medical records can be otherwise performed.

In another variation of Block S150, the notification can provide advice to the patient, based upon the analysis, to avoid contact with people identified in Blocks S130 and S140 to produce degradation in the patient's cardiovascular state, based upon the analysis. In another example, the notification can provide advice to the patient, based upon the analysis, to avoid travel to certain locations identified in Blocks S130 and S140 to produce degradation in the patient's cardiovascular state. In another example, the notification can notify the user of a period of lack of social contact, and can additionally or alternatively set reminders for the patient to contact entities identified to have a positive impact on the patient's cardiovascular health. In another example, the notification can provide the user with incentives (e.g., coupons, discounts) to increase his/her mobility or social contact, thereby preventing degradation in cardiovascular health. The notification can additionally or alternatively be provided as described in U.S. application Ser. No. 13/969,339, entitled "Method for Modeling Behavior and Health Changes", and/or in any other suitable manner.

However, providing a cardiovascular health-related notification can be performed in any manner.

3.6 Providing a Cardiovascular Therapeutic Intervention

In some variations, the method 100 can additionally or alternatively include Block S160, which recites: automatically providing a cardiovascular therapeutic intervention for the patient. Block S160 functions to promote interventions configured to improve a patient's cardiovascular health state.

Regarding Block S160, a cardiovascular therapeutic intervention is preferably configured to improve one or more cardiovascular health metrics for a patient. A cardiovascular therapeutic intervention can include any one or more of: health professional provision, sensory stimulus modification, notifications, controlling a patient device, treatment recommendations, and/or any other suitable intervention.

Figure 6:
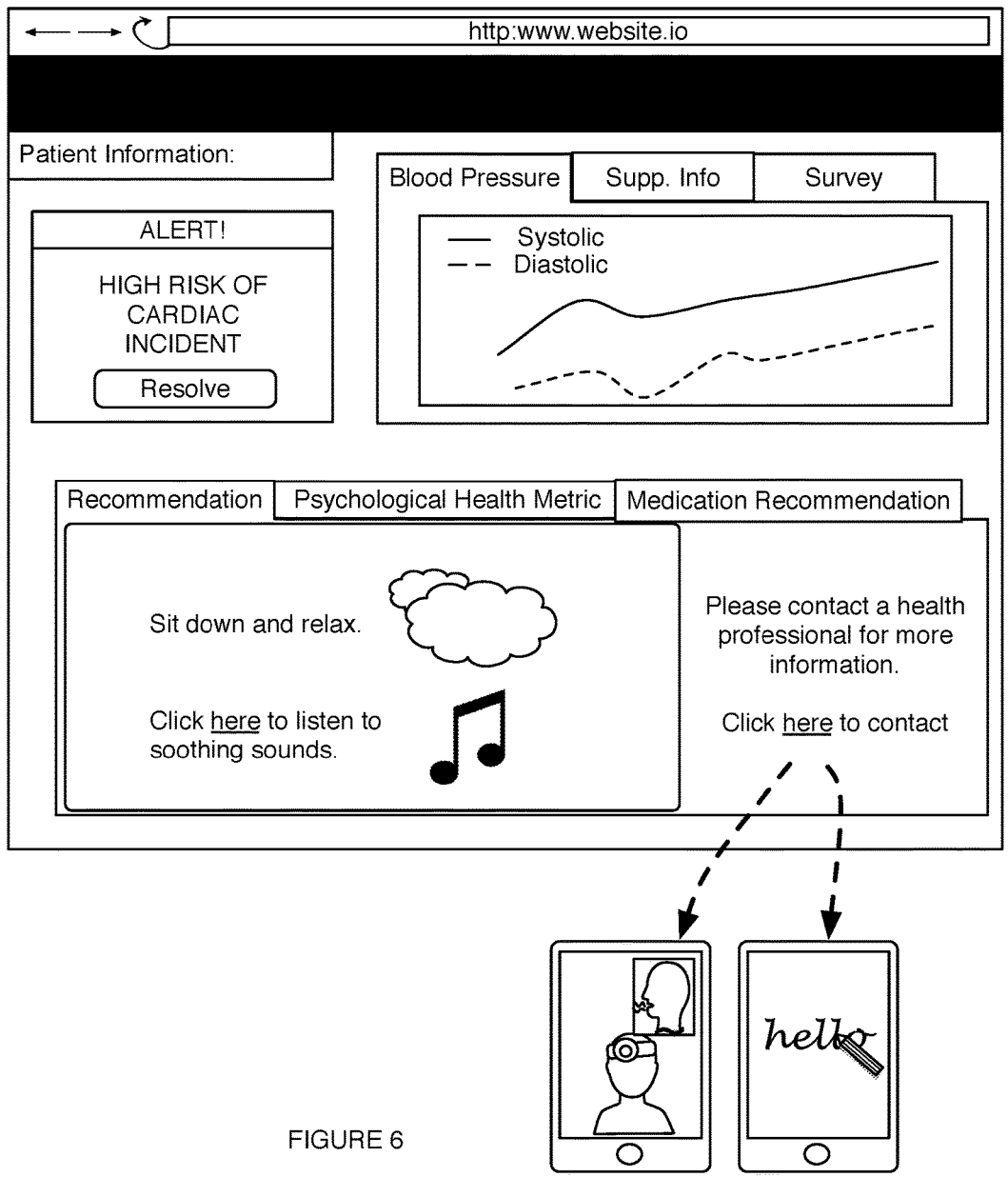
FIG. 6 is a graphical representation of a patient digital interface.

In a variation, as shown in FIG. 6, Block S160 includes facilitating health professional (e.g., a nurse, care provider, a pharmacist, a pharmacologist, a health coach, a therapist, a nutritionist, a dietician, an exercise instructor, a personal trainer, etc.) provision. Facilitating health professional provision can include facilitating telemedicine communications (e.g., via establishing a wireless communicable link between a patient and a health professional; via providing a digital communication venue between the patient and health professional, etc.), appointment scheduling, on-demand health professional service (e.g., house visits, etc.), and/or any suitable mechanism of connecting one or more health professionals with a patient. In an example, the method 100 can include providing a cardiovascular therapeutic intervention, where the cardiovascular therapeutic intervention is a digital telemedicine communication with a health professional, and where providing the cardiovascular therapeutic intervention includes automatically establishing a wireless communicable link with a health professional mobile computing device associated with the health professional, and facilitating the digital telemedicine communication using the wireless communicable link. However, facilitating health professional provision can be performed in any manner analogous to embodiments, variations, and examples of which are described in U.S. application Ser. No. 15/005,923, entitled "Method for Providing Therapy to an Individual" and filed on 25 Jan. 2016, which is herein incorporated in its entirety by this reference.

In another variation, as shown in FIG. 6, Block S160 includes modifying a sensory stimulus presented to the patient. Sensory stimuli can be directed towards a patient's sight, hearing, touch, smell, taste, and/or any suitable senses. Modifying a sensor stimulus can include presenting images, video, audio, multimedia, and/or any other suitable stimuli configured to improve cardiovascular health. In an example, Block S160 can include controlling an application executing on a patient mobile computing device to present the sensory stimulus. In a specific example, the method 100 can include providing a cardiovascular therapeutic intervention in the form of an audio therapy configured to improve the cardiovascular health metric, and wherein providing the cardiovascular therapeutic intervention includes controlling the mobile computing device to emit the audio therapy. In another example, Block S160 can include transforming a digital user interface associated with the patient mobile computing device. Transforming the digital user interface can include one or more of: modifying a color scheme, modifying a lighting parameter, highlighting a cardiovascular-related notification, highlighting options to initiate a particular cardiovascular therapeutic intervention, and/or any other suitable modifications. However, modifying a sensory stimulus can be performed in any manner.

In another variation, as shown in FIG. 4, Block S160 can include communicating with a patient device (e.g., a cardiovascular device, a mobile computing device, a smart appliance, etc.). Communicating with the patient device can include: modifying the configuration settings of the patient device (e.g., through sending a request to the patient device), sending a notification (e.g., cardiovascular-related notification) to the patient device (e.g., for presentation at the patient device), controlling the patient device to collect additional data (e.g., at a cardiovascular monitoring device), modifying the programming of a patient device (e.g., a programmable pacemaker, etc.), and/or any other suitable action.

In examples of this variation, Block S160 can include providing a cardiovascular therapeutic intervention at a cardiovascular therapy device. In a specific example, Block S160 can include modifying the configuration settings of an automatic medication dispenser to recommend consumption of a medication at specific times (e.g., based on optimal times for improving cardiovascular health, in anticipation of an activity that may cause angina, in order to relieve an episode of angina, based on GPS location data such as when the user is home, when digital communication behaviors suggest a lack of treatment adherence, etc.). In another specific example, Block S160 can include transmitting one or more cardiovascular parameters (e.g., cardiovascular health metrics) to a smart exercise device for developing a fitness program personalized to the patient (e.g., tailored to patient heart rate patterns, personalized to prompt exercise at a difficult suitable for the patient's cardiovascular health, etc.). In another example, Block S160 includes automatically programming a pacemaker (e.g., pacing modes, rate settings, pulse amplitude, rate adaptive features, etc.) to optimize heart rhythm control functionality for the patient based on one or more cardiovascular parameters. In another specific example, communication with the patient device can improve the functioning of the patient device, such as through optimizing configuration of a cardiovascular therapy device in improving cardiovascular health, thus improving the efficiency (e.g., battery usage, processing, etc.) of the patient device. However, controlling operation of cardiovascular therapy devices can be performed in any manner.

In other examples of this variation, Block S160 can include providing a cardiovascular therapeutic intervention at one or more cardiovascular monitoring devices. In a specific example, Block S160 can include communicating with a heart rate monitor to initiate data collection in response to generating cardiovascular health metrics indicating irregular heart rate. In another specific example, Block S160 can include transmitting a cardiovascular-related notification to a wearable fitness tracker fo presentation to the patient. However, communicating with cardiovascular monitoring devices can be performed in any manner.

In other examples of this variation, Block S160 can include providing a cardiovascular therapeutic intervention at one or more smart appliances. In a specific example, Block S160 can include automatically transmitting a request to a smart thermometer to modify the temperature based on one or more cardiovascular parameters (e.g., reducing temperature of a room in response to a above average heart rate of the patient). In another specific example, Block S160 can include controlling operation of a smart lighting system (e.g., Phillips Hue™, LIFX™, etc.) to emit light at a lighting setting determined based on one or more patient cardiovascular parameters (e.g., changing harsh lighting to soothing lighting in response generating a cardiovascular health metric indicating high blood pressure). In another specific example, Block S160 can include modifying the configuration settings of a smart cooking appliance (e.g., a smart oven) to recommend heart-healthy meals. In another specific example, Block S160 can include controlling a smart television to recommend and/or record television programs with a focus on physical activity (e.g. healthy cooking shows, travel channels, etc.). However, communicating with a smart appliance and/or any suitable patient device can be performed in any manner.

Figure 7:
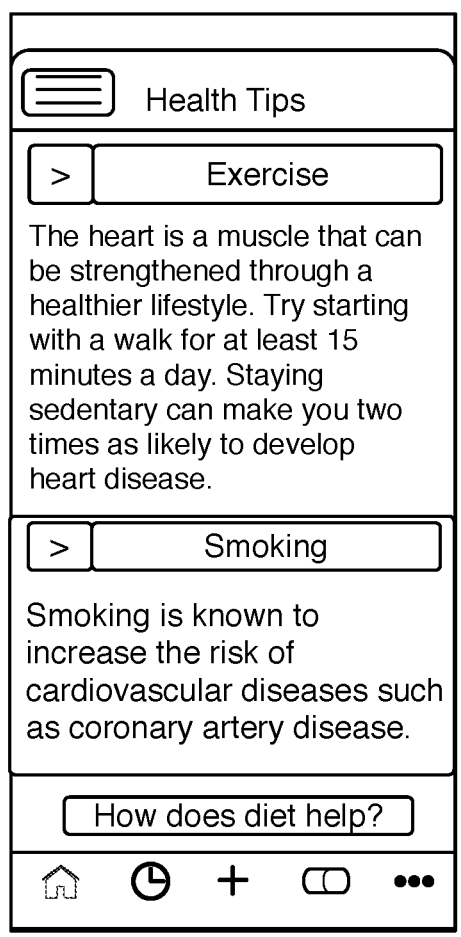
FIG. 7 is a graphical representation of a health tip.

As shown in FIG. 7, in another variation, Block S160 can include providing a cardiovascular therapeutic intervention in the form of a cardiovascular-related notification (e.g., a notification in Block S150). Notifications designed for cardiovascular therapy can include health tips, notifications related to a treatment regimen (e.g., a reminder to consume a medication), notifications prompting physical activity (e.g., games prompting physical activity, physical activities based on mobility behavior supplementary data, etc.) educational tips (e.g., correlations between cardiovascular disease and lifestyle choices that the patient is making, etc.), and/or any suitable information. In an example, the method 100 can include providing a cardiovascular therapeutic intervention, where the intervention is a cardiovascular-related notification, and where automatically providing the cardiovascular therapeutic intervention includes automatically providing the cardiovascular-related notification at a cardiovascular device associated with the patient. However, providing a cardiovascular therapeutic notification can be performed in any manner.

In another variation, as shown in FIG. 6, Block S160 can include generating and/or providing a treatment recommendation. A treatment recommendation can include any one or more of a medication recommendation (e.g., beta blockers, lipid-lowering agents, alpha-2 adrenergic agonists, nitroglycerin, etc.), medical procedure recommendations (e.g., heart surgery, angioplasty, atherectomy, cardiomyoplasty, transplant, ablation, stent, revascularization, etc.), and/or any other suitable medical recommendation. Generating a treatment recommendation can be derived from at least one of a passive dataset, an active dataset, and an output of a cardiovascular health predictive model. However, providing a treatment recommendation can be performed in any manner.

In Block S160, providing a cardiovascular therapeutic intervention is preferably in real-time (e.g., in response to a patient request for a therapeutic intervention, during the time period in which a log of use dataset, supplementary dataset, and/or survey dataset is collected, during a time period in which the patient is experiencing a cardiovascular disease-related symptom, etc.). Further, providing a cardiovascular therapeutic intervention is preferably in response to satisfaction of a threshold condition (e.g., in Block S131, S132, S133). For example, Block S160 can include, in response to the cardiovascular health metric satisfying a cardiovascular health threshold condition, automatically providing a cardiovascular therapeutic intervention at a cardiovascular device for the patient.

In a variation, Block S160 can include activating a cardiovascular therapeutic intervention during a time period that is determined based on cardiovascular health metric values corresponding to different time periods during the day. In an example, generated cardiovascular health metrics (e.g., in Block S130) can indicate poorer cardiovascular health during time periods of infrequent digital communication, and cardiovascular therapeutic interventions can be promoted during these time periods.

In another variation, Block S160 can include promoting a cardiovascular therapeutic intervention at a time determined based on a supplementary dataset. For example, a cardiovascular therapeutic intervention can be provided during a time period in which a cardiovascular monitoring device supplementary dataset indicates an above-average heart rate. In this example, the cardiovascular therapeutic intervention, can for example, provide a stress-relieving sensory stimulus (e.g., soothing sounds, a relaxing video, etc.) at a patient device.

In another variation, Block S160 can include providing a set of cardiovascular therapeutic interventions spread out over a time period. Provided types of cardiovascular therapeutic intervention can be updated based on patient feedback (e.g., datasets collected in Blocks S110, S120, S125 during a time period following a therapeutic intervention), and/or any suitable dataset. In an example, the method 100 can include providing a first cardiovascular therapeutic intervention, receiving a log of use dataset associated with a time period subsequent to provision of the first cardiovascular therapeutic intervention; selecting a second cardiovascular therapeutic intervention based on the log of use dataset; and providing the second cardiovascular therapeutic intervention, where the first and second cardiovascular therapeutic interventions are distinct.

In another variation, Block S160 can include providing a cardiovascular therapeutic intervention at a time determined by the log of use dataset. For example, a health tip prompting physical activity can be pushed to a patient mobile computing device during a time period in which the patient transmits digital communications describing free time and/or a lack of physical activities.

However, providing a cardiovascular therapeutic intervention can be performed at any suitable time.

In relation to Block S160, cardiovascular therapeutic interventions can be provided at a patient device and/or any suitable device (e.g., a health professional device). Generation and/or provision of the therapeutic intervention(s) can thus be facilitated through one or more of: an application executing on an electronic device (e.g., mobile device, tablet, personal computer, head-mounted wearable computing device, wrist-mounted wearable computing device, etc.) of the patient, a web application accessible through an internet browser, an entity (e.g., caretaker, spouse, healthcare provider, relative, acquaintance, etc.) trained to provide the therapy regimen, and in any other suitable manner. In examples, portions of a therapy regimen can be delivered in-app through the mobile communication device, and/or interactions between the patient and a therapeutic entity can be established using modules of the computing system. Providing cardiovascular therapeutic interventions can be performed through communicable links between devices, API requests, human guidance, healthcare provider interactions (e.g., therapeutic sessions with a counselor), pharmaceutical compound distributors, mobile application implemented methods, web browser-facilitated methods, and any other suitable avenue of therapy provision. The therapeutic interventions of Block S160 can additionally or alternatively be provided in a manner similar to that described in U.S. application Ser. No. 13/969,339, entitled "Method for Modeling Behavior and Health Changes", with therapy/treatment efficacy analyzed by a treatment regimen model and/or a treatment efficacy model. Cardiovascular therapeutic interventions can, however, be provided in any other suitable manner or assessed in any other suitable manner, and/or through any suitable mechanism.

However, providing a cardiovascular therapeutic intervention can be performed in any suitable manner.

3.7 Generating a Psychological Health Metric

The method 100 can optionally include Block S170, which recites: generating a psychological health metric. Block S170 functions to determine values of one or more psychological health metrics in association with at least one time period.

Regarding Block S170, a psychological health metric preferably indicates a psychological health of the patient regarding any one or more of: psychosis, depression, bipolar disorder, anxiety, schizophrenia, and/or any suitable mental condition (e.g., a condition described in the Diagnostic and Statistical Manual of Mental Disorders). Additionally or alternatively, a psychological health metric can indicate a patient's mood, emotions, well-being, and/or other suitable psychological-related metric. However, a psychological health metric can indicate any suitable information.

For Block S170, generating a psychological health metric is preferably based on a log of use dataset (e.g., collected in Block S110). In an example, Block S170 can include generating a psychological health metric from a psychological health predictive model and a log of use dataset. Log of use data used in generating a psychological health metric can be identical, different, and/or overlapping with log of use data used in generating a cardiovascular health metric. For example, the method 100 can include generating a cardiovascular health predictive model from a first log of use dataset; extracting a cardiovascular health metric from at least one of an output of the cardiovascular health predictive model and the first log of use dataset; and generating a psychological health metric from a second log of use dataset, where the first and second log of use datasets are identical. Additionally or alternatively, generating a psychological health metric can be determined from any data usable in generating a cardiovascular health metric (e.g., supplementary data, survey data, etc.), and/or any suitable data. For example, generating a psychological health metric can be based on digital communication behavior features (e.g., determined from the log of use dataset) and a correlation between a travel metric (e.g., derived from a mobility behavior supplementary dataset) and psychological health of the patient.

Regarding Block S170, generating a psychological health metric can be performed before, contemporaneously, and/or after generating a cardiovascular health metric S130, but can otherwise be performed at any time.

Additionally or alternatively, extracting a psychological health metric S170 can include any elements described in U.S. application Ser. No. 14/839,232 entitled "Method for modeling Behavior and Psychotic Disorders" and filed 1 Oct. 2015, U.S. application Ser. No. 14/839,053 entitled "Method for Modeling Behavior and Depression State" and filed 28 Aug. 2015, and U.S. application Ser. No. 13/969,339 entitled "Method for Modeling Behavior and Health Changes" and filed 16 Aug. 2014, each of which are incorporated herein in their entirety by this reference; however, Block S170 can be performed in any suitable manner.

3.8 Generating a Psychological Therapeutic Intervention

The method 100 can optionally include Block S175, which recites: generating a psychological therapeutic intervention. Block S175 functions to promote interventions configured to improve a patients' psychological health state.

Regarding Block S175, a psychological therapeutic intervention preferably improves one or more psychological health metrics associated with a user. A psychological therapeutic intervention can include any of the cardiovascular therapeutic interventions described in Block S160 and/or notifications described in Block S150. In an example, Block S175 can include providing, to the patient at the mobile computing device, a psychological health-related notification based on a psychological health metric; and providing a health-related notification to the patient at the mobile computing device, wherein the health-related notification is based on a cardiovascular health metric and the psychological health metric.

In relation to Block S175, providing a psychological therapeutic intervention is preferably performed in response to satisfaction of a psychological health threshold condition by a parameter of at least one of a log of use dataset, a supplementary dataset, a survey dataset, an output of a psychological health predictive model, and/or any suitable data. In variations, comparisons of psychological health parameters to threshold conditions can be performed in any manner analogous to Block S131, S132, and S133. Additionally or alternatively, Block S175 can be performed before, during, and/or after providing a cardiovascular therapeutic intervention S160. In a variation, the method 100 can include providing a therapeutic intervention configured to improve both the cardiovascular health (e.g., as indicated by a cardiovascular health metric) and psychological health (e.g., as indicated by a psychological health metric) of a patient.

Regarding Block S175, a psychological therapeutic intervention can be provided through any suitable source (e.g., sources described as capable of providing a cardiovascular therapeutic intervention in Block S160). In an example, Block S175 can include, in response to the psychological health metric satisfying a psychological health threshold condition, automatically providing a psychological therapeutic intervention at the cardiovascular device for the patient.

In a variation, Block S175 can include presenting a psychological health-related notification at a patient device. The psychological health-related notification can include psychological health tips (e.g., cognitive distortions, psychological health facts, etc.), information related to psychological health metrics, notifications prompting activities for promoting psychological health, etc. In a specific example, presenting a psychological health-related notification can include prompting a patient to take a walk through a nature setting, where the notification can be configured to improve both psychological and cardiovascular health. However, presenting a psychological health-related notification can be performed in any manner.

In another variation, Block S175 can include modifying a sensory stimulus presented to the user at a patient device. For example, Block S175 can include modifying the configuration settings at an activity tracking device to provide alerts that are less critical of patient performance in response to generating psychological health metrics indicating patient insecurity. In another example, Block S175 can include transforming a user interface of a cardiovascular device to a softer color palette, in response to psychological health metrics indicating patient anxiety. In another example, Block S175 can include presenting a media file (e.g., meditation video, a mindfulness audio exercise, etc.) to the patient at a patient device. However, modifying one or more sensory stimuli can be performed in any manner.

In another variation, Block S175 can include promoting a psychological therapeutic intervention at a cardiovascular device. For example, Block S175 can include applying electrical brain stimulation at a pair of smart glasses with heart rate monitoring functionality. In another example, Block S175 can include transmitting psychological health metrics to a smart exercise machine for developing a fitness program tailored for improving mental health of a patient (e.g., a program with an appropriate intensity for a patient's mental status, a program tailored for neurogenesis, etc.). However, promoting a psychological therapeutic intervention at a cardiovascular device can be performed in any suitable manner.

In another variation, Block S175 can include providing a psychological therapeutic intervention at one or more smart appliances. For example, Block S175 can include selecting color parameters of a smart lighting system, the color parameters configured to reduce stress of the patient, and additionally reduce blood pressure. In another example, Block S175 can include modifying configuration settings of a smart television to discourage television programs with violence involved, which can additionally reduce average heart rate. In another example, Block S175 can include communicating with a smart oven to recommend brain-healthy recipes (e.g., foods including omega-3 fatty acids), which can additionally be healthy for the cardiovascular system. However, promoting a psychological therapeutic intervention at a smart appliance can be performed in any suitable manner.

Additionally or alternatively, providing a psychological therapeutic intervention S175 can include any elements described in U.S. application Ser. No. 14/839,232 entitled "Method for modeling Behavior and Psychotic Disorders" and filed 1 Oct. 2015, U.S. application Ser. No. 14/839,053 entitled "Method for Modeling Behavior and Depression State" and filed 28 Aug. 2015, and U.S. application Ser. No. 13/969,339 entitled "Method for Modeling Behavior and Health Changes" and filed 16 Aug. 2014, each of which are incorporated herein in their entirety by this reference; however, Block 8175 can be performed in any suitable manner.

3.9 Updating a Predictive Model

The method 100 can optionally include Block S180, which recites: updating a predictive model. Block S180 functions to update one or more cardiovascular health models and/or psychological health models for providing updated cardiovascular health metrics and/or psychological health metrics.

Block S180 preferably includes updating one or more predictive models with an additional log of use dataset (e.g., a log of used dataset associated with a time period subsequent to generating an initial predictive model). Additionally or alternatively, a predictive model can be updated with additional supplementary data (e.g., supplemental data collected subsequent to provision of a therapeutic intervention), additional survey data (e.g., a patient response to a survey administered after providing a therapeutic intervention), and/or any other suitable information.

However, any suitable predictive model can be updated with any suitable information at any suitable time.

The method 100 can, however, include any other suitable blocks or steps configured to model behavior and cardiovascular health, and/or improve a cardiovascular state of a patient. Furthermore, as a person skilled in the art will recognize from the previous detailed description and from the figures and claims, modifications and changes can be made to the method 100 without departing from the scope of the method 100.

4. System.

Figure 5:
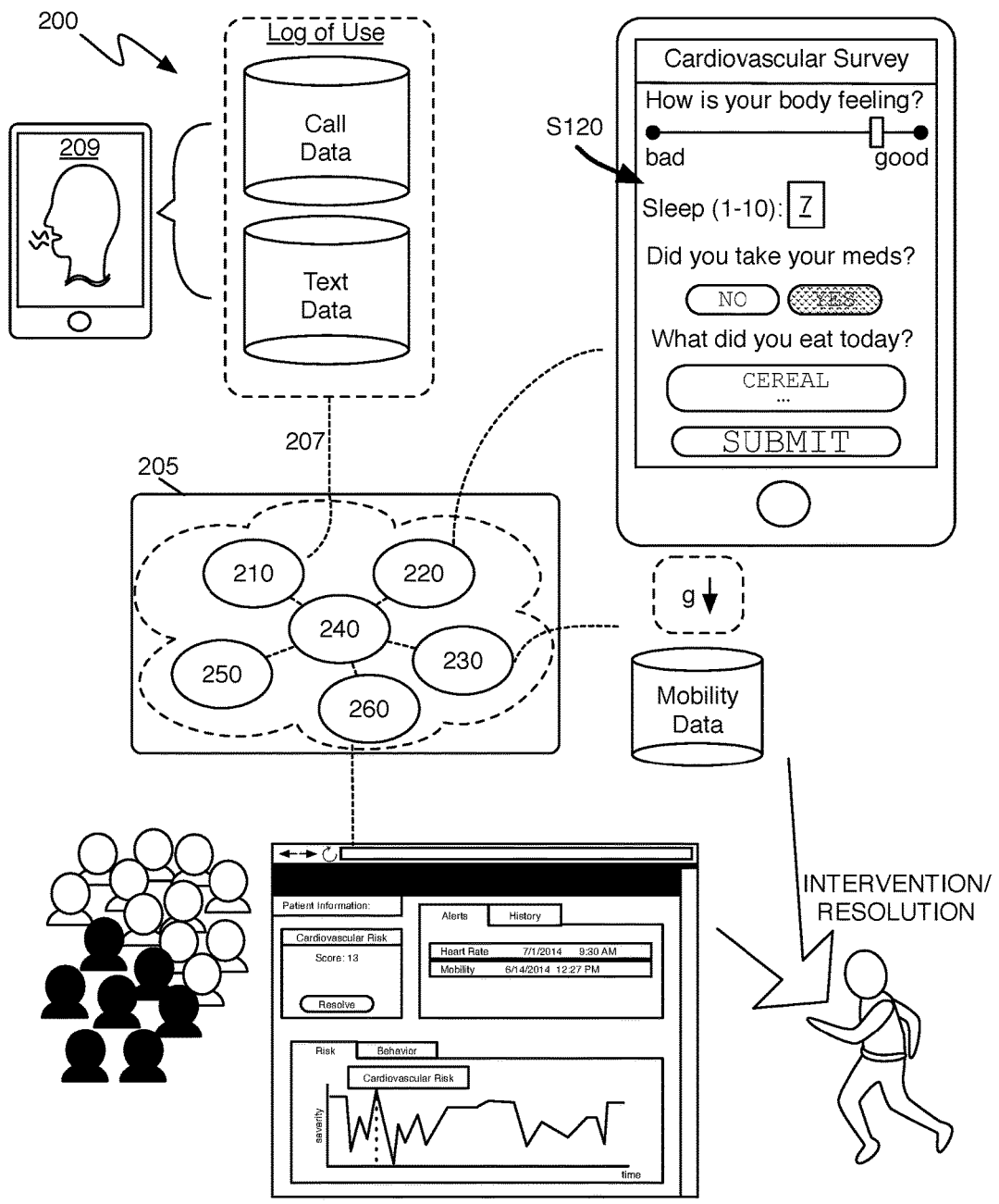
FIG. 5 is a schematic representation of a variation of an embodiment of the method.

As shown in FIG. 5, a system 200 for modeling behavior and cardiovascular health of a patient includes: a processing system 205 including: an interface 207 with a native data collection application executing on a mobile computing device 209 of the patient; a first module 210 configured to access a log of use of a native communication application coupled to the native data collection application on the mobile computing device by the patient within a time period; a second module 220 configured to receive a supplementary dataset characterizing activity of the patient in association with the time period; a third module 230 configured to receive a survey dataset including responses, to at least one of a set of cardiovascular evaluation surveys, associated with a set of time points of the time period, from the patient; a fourth module 240 configured to extract a cardiovascular health metric from at least one of the log of use, the survey dataset, and the supplementary dataset; a fifth module 250 configured to provide a cardiovascular-related notification; and a sixth module 260 configured to provide a cardiovascular therapeutic intervention. The system 200 can incorporate, at least in part, embodiments, variations, and examples of elements of the system described in U.S. application Ser. No. 13/969,339 entitled "Method for Modeling Behavior and Health Changes" and filed on 16 Aug. 2013. Additionally or alternatively the system 200 can include any one or more of any suitable patient device, which can perform any suitable portion of the method 100. The patient device can include any one or more of a cardiovascular device (e.g., cardiovascular therapy device, cardiovascular monitoring device, etc.), a mobile computing device (e.g., a smartphone, a tablet, smart watch, laptop, etc.), a smart appliance (e.g., a smart lighting system, a smart thermometer, a smart oven, a smart media device, etc.), and/or any other suitable patient device. A cardiovascular therapy device can include one or more of a defibrillator (e.g., an implantable cardioverter defibrillator, automated external defibrillator, etc.), pacemakers, prosthetic heart valves, stents, ventricular assist devices, cardiac ablation catheters, cardiac angioplasty devices, exercise device, and/or other suitable device for provisioning cardiovascular therapy. A cardiovascular monitoring device can include one or more of: a cardiac loop recorder (e.g., for recording heart rhythm), heart rate monitor, blood pressure monitor, hemodynamic monitor, biosignal detector device (e.g., electrooculography, electromyography, electrocardiography, galvanic skin response, magnetoencephalogram, etc.), weight scale (e.g., a smart weight scale), and/or other suitable device for monitoring cardiovascular activity.

The system 200 functions to perform at least a portion of the method 100 described in Section 1 above, but can additionally or alternatively be configured to perform any other suitable method for modeling behavior and cardiovascular health of a patient. The system 200 is preferably configured to facilitate reception and processing of a combination of active data (e.g., survey responses) and passive data (e.g., unobtrusively collected communication behavior data, mobility data, etc.), but can additionally or alternatively be configured to receive and/or process any other suitable type of data. As such, the processing system 205 can be implemented on one or more computing systems including one or more of: a cloud-based computing system (e.g., Amazon EC3), a mainframe computing system, a grid-computing system, and any other suitable computing system. Furthermore, reception of data by the processing system 205 can occur over a wired connection and/or wirelessly (e.g., over the Internet, directly from a natively application executing on an electronic device of the patient, indirectly from a remote database receiving data from a device of the patient, etc.).

The processing system 205 and data handling by the modules of the processing system 205 are preferably adherent to health-related privacy laws (e.g., HIPAA), and are preferably configured to privatize and/or or anonymize patient data according to encryption protocols. In an example, when a patient installs and/or authorizes collection and transmission of personal communication data by the system 200 through the native data collection application, the native application can prompt the patient to create a profile or account. In the example, the account can be stored locally on the patient's mobile computing device 209 and/or remotely. Furthermore, data processed or produced by modules of the system 200 can be configured to facilitate storage of data locally (e.g., on the patient's mobile computing device, in a remote database), or in any other suitable manner. For example, private health-related patient data can be stored temporarily on the patient's mobile computing device in a locked and encrypted file folder on integrated or removable memory. In this example, the patient's data can be encrypted and uploaded to the remote database once a secure Internet connection is established. However, patient data can be stored on any other local device or remote data in any other suitable way and transmitted between the two over any other connection via any other suitable communication and/or encryption protocol. As such, the modules of the system 200 can be configured to perform embodiments, variations, and examples of the method 100 described above, in a manner that adheres to privacy-related health regulations. Mobile computing devices, cardiovascular devices (e.g., monitoring devices, therapy devices), smart appliance devices and/or other non-generalized computing systems can be communicably connected (e.g., wired, wirelessly) through any suitable communication networks. For example, a mobile computing device can collect a log of use dataset and a survey dataset, a cardiovascular device can collect a supplementary dataset, a remote server can receive the datasets from the corresponding devices, and the remote server can generate one or more cardiovascular health metrics and promote one or more cardiovascular therapeutic intervention (e.g., through communication with the mobile computing device and/or cardiovascular device). However, the system 200 can include any suitable configuration of non-generalized computing systems connected in any combination to one or more communication networks.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for therapeutic intervention provision for cardiovascular health of a patient, the method comprising:
    receiving a first log of use dataset associated with patient digital communication behavior at a mobile computing device, wherein the first log of use dataset corresponds to a time period;
    receiving a supplementary dataset associated with the mobile computing device, wherein the supplementary dataset corresponds to the time period;
    generating a cardiovascular health predictive model based upon the first log of use dataset and the supplementary dataset;
    extracting a cardiovascular health metric from at least one of an output of the cardiovascular health predictive model, the first log of use dataset, and the supplementary dataset, wherein the cardiovascular health metric is associated with the time period; and
    in response to the cardiovascular health metric satisfying a cardiovascular health threshold condition, automatically administering a cardiovascular therapeutic intervention at a cardiovascular device for the patient, for improvement of the cardiovascular health of the patient.

2. The method of claim 1, further comprising:
    presenting a cardiovascular evaluation digital survey to the patient at the mobile computing device; and
    generating a survey dataset from a patient response to the cardiovascular evaluation digital survey,
    wherein extracting the cardiovascular health metric comprises extracting the cardiovascular health metric from at least one of the survey dataset, the output of the cardiovascular health predictive model, the first log of use dataset, and the supplementary dataset.

3. The method of claim 2, further comprising:
    assigning the patient to a cardiovascular subgroup of a set of cardiovascular subgroups, based on the survey dataset to the cardiovascular evaluation digital survey; and
    retrieving a subgroup predictive model corresponding to the cardiovascular subgroup, wherein generating the cardiovascular health metric is in response to retrieving the subgroup predictive model, and wherein the cardiovascular health predictive model comprises the subgroup predictive model.

4. The method of claim 1, wherein the cardiovascular therapeutic intervention comprises a cardiovascular-related notification, and wherein automatically providing the cardiovascular therapeutic intervention comprises automatically providing the cardiovascular-related notification at the cardiovascular device.

5. The method of claim 1, wherein the cardiovascular health metric comprises at least one of a blood pressure metric, a heartbeat metric, and a respiration metric.

6. The method of claim 1, wherein the first log of use dataset indicates at least one of phone call-related data and text messaging data.

7. The method of claim 1, wherein the cardiac device comprises the mobile computing device.

8. The method of claim 1, further comprising:
    generating a psychological health metric from a psychological health predictive model and a second log of use dataset; and
    providing a health-related notification to the patient at the mobile computing device, wherein the health-related notification is based on at least one of the cardiovascular health metric and the psychological health metric.

9. The method of claim 8, wherein the first and the second log of use datasets are identical.

10. The method of claim 8, further comprising: in response to the psychological health metric satisfying a psychological health threshold condition, automatically providing a psychological therapeutic intervention at the cardiovascular device for the patient.

11. A method for therapeutic intervention provision for cardiovascular health of a patient, the method comprising:
    receiving a log of use dataset associated with patient digital communication behavior at a mobile computing device, wherein the log of use dataset corresponds to a time period;
    determining digital communication behavior features based on the log of use dataset;
    generating a cardiovascular health metric from the digital communication behavior features, wherein the cardiovascular health metric indicates the cardiovascular health of the patient during the time period; and
    in response to generating the cardiovascular health metric, administering a cardiovascular therapeutic intervention to the patient at a cardiovascular device, wherein the cardiovascular therapeutic intervention is based on the cardiovascular health metric, for improvement of the cardiovascular health of the patient.

12. The method of claim 11, wherein administering the cardiovascular therapeutic intervention comprises: in response to the cardiovascular health metric satisfying a cardiovascular health threshold condition, automatically administering the cardiovascular therapeutic intervention for the patient at the mobile computing device.

13. The method of claim 12, wherein the cardiovascular therapeutic intervention comprises an audio therapy configured to improve the cardiovascular health metric, and wherein providing the cardiovascular therapeutic intervention comprises controlling the mobile computing device to emit the audio therapy.

14. The method of claim 11, wherein the cardiovascular therapeutic intervention comprises a digital telemedicine communication with a health professional, and wherein providing the cardiovascular therapeutic intervention comprises:
  automatically establishing a wireless communicable link with a health professional computing device associated with the health professional; and
  facilitating the digital telemedicine communication using the wireless communicable link.

15. The method of claim 11, further comprising:
  receiving a patient mobility behavior supplementary dataset comprising a travel metric indicating a distance traveled by the patient during the time period, wherein the patient mobility behavior supplementary dataset corresponds to the time period,
  wherein generating the cardiovascular health metric comprises generating the cardiovascular health metric from at least one of the patient mobility behavior supplementary dataset and the digital communication behavior features.

16. The method of claim 11, further comprising:
  receiving a heart rate supplementary dataset collected at a heart rate sensor of a cardiovascular device, wherein the heart rate supplementary dataset corresponds to the time period,
  wherein generating the cardiovascular health metric comprises generating the cardiovascular health metric from the digital communication behavior features and the heart rate supplementary dataset.

17. The method of claim 11, wherein the time period is subsequent to patient consumption of a cardiovascular medication, and wherein generating the cardiovascular health metric comprises generating a treatment response metric indicating treatment response to the cardiovascular medication during the time period.

18. The method of claim 17, further comprising:
  presenting a cardiovascular evaluation digital survey to the patient at the mobile computing device;
  generating a survey dataset based on a patient response to the cardiovascular evaluation digital survey; and
  identifying cardiovascular medication data associated with the cardiovascular medication, based on the survey dataset,
  wherein generating the treatment response metric is based on the digital communication behavior features and the cardiovascular medication data.

19. The method of claim 11, wherein the cardiac device comprises the mobile computing device.

20. The method of claim 11, further comprising:
  in response to the cardiovascular health metric satisfying a cardiovascular health threshold condition, automatically establishing a wireless communicable link with a cardiovascular device associated with the patient;
  delivering, through the wireless communicable link, a cardiovascular therapeutic intervention to the patient at the cardiovascular device.

21. The method of claim 11, wherein providing the cardiovascular therapeutic intervention comprises providing a haptic alert to the patient at the cardiovascular device in response to the cardiovascular health metric satisfying a cardiovascular threshold condition.

* * * * *

UNITED STATES PATENT AND TRADEMARK OFFICE
CERTIFICATE OF CORRECTION

PATENT NO.         : 10,265,028 B2
APPLICATION NO.    : 15/245571
DATED              : April 23, 2019
INVENTOR(S)        : Sai Moturu and Anmol Madan Page 1 of 1

It is certified that error appears in the above-identified patent and that said Letters Patent is hereby corrected as shown below:

In the Claims

Column 36, Line 37, Claim 10 after "comprising:", insert --¶--
Column 36, Line 61, Claim 12 after "comprising:", insert --¶--

Signed and Sealed this
Third Day of March, 2020

Andrei Iancu
*Director of the United States Patent and Trademark Office*